United States Patent [19]

Thome et al.

[11] Patent Number: 5,776,080

[45] Date of Patent: Jul. 7, 1998

[54] SHAFT MOVEMENT CONTROL APPARATUS

[75] Inventors: Scott Thome, Waite Park; Kevin Klitz, Plymouth; Janet L. Jacobsen, Maple Grove, all of Minn.; Kevin Kang, Mesa, Ariz.; Roger Hastings, Maple Grove, Minn.

[73] Assignee: SciMed Life Systems, Inc., Maple Grove, Minn.

[21] Appl. No.: 850,650

[22] Filed: May 2, 1997

Related U.S. Application Data

[63] Continuation of Ser. No. 369,190, Jan. 5, 1995, abandoned, which is a continuation-in-part of Ser. No. 48,492, Apr. 16, 1993, Pat. No. 5,555,893, which is a continuation-in-part of Ser. No. 929,083, Aug. 12, 1992, Pat. No. 5,623,943.

[51] Int. Cl.$^6$ ...................................................... A61B 5/00
[52] U.S. Cl. ...................................................... 600/585
[58] Field of Search .................................. 128/657, 658, 128/772; 604/95, 280–283

[56] References Cited

U.S. PATENT DOCUMENTS

| | | |
|---|---|---|
| 3,358,676 | 12/1967 | Frei et al. . |
| 3,674,014 | 7/1972 | Tillander . |
| 3,722,505 | 3/1973 | Kolin . |
| 3,941,119 | 3/1976 | Corrales . |
| 3,961,632 | 6/1976 | Moossun . |
| 4,054,128 | 10/1977 | Seufert et al. ............... 128/4 |
| 4,077,412 | 3/1978 | Moossun . |
| 4,134,405 | 1/1979 | Smit . |
| 4,162,679 | 7/1979 | Reenstierna . |
| 4,244,362 | 1/1981 | Anderson . |
| 4,249,536 | 2/1981 | Vega . |
| 4,315,509 | 2/1982 | Smit . |
| 4,671,287 | 6/1987 | Fiddian-Green . |

(List continued on next page.)

FOREIGN PATENT DOCUMENTS

| | | |
|---|---|---|
| 0 416 734 A1 | 7/1990 | European Pat. Off. . |
| 0 415 332 A1 | 8/1990 | European Pat. Off. . |
| 0 409 372 A1 | 1/1991 | European Pat. Off. . |
| 0 232 968 B1 | 9/1992 | European Pat. Off. . |
| 2 245 495 | 1/1992 | United Kingdom . |
| WO 81/02109 | 8/1981 | WIPO . |
| WO 89/07958 | 9/1989 | WIPO . |
| WO 93/15786 | 8/1993 | WIPO . |
| WO 94/03229 | 2/1994 | WIPO . |

OTHER PUBLICATIONS

J. Driller, W. Casarella, T. Asch, S.K. Hilal; *The POD Bronchial Catheter*, IEEE Transactions on Magnetics, vol. Mag–6, No. 2, pp. 353–355, Jun., 1970.

A. Snider; *New Techniques Used in Lung Biopsy*, The Washington Post, p. E16, Thursday, Dec. 4, 1969.

D. Montgomery and R. Weggel; *Magnetic Forces for Medical Applications*, IEEE Transcactions on Magnetics, p. 374, Jun. 1970.

D. Montgomery, J. Hale, N. Pierce and S. Yodh; *A Magnetically Guided Catheter System for Intracranial Use in Man*, IEEE Transactions on Magnetics, pp. 374–375, Jun. 1970.

H. Tillander; *Selective Angiography with a Catheter Guided by a Magnet*, IEEE Transactions on Magnetics, vol. Mag–6, No. 2, pp. 355–358, Jun. 1970.

*Primary Examiner*—Max Hindenberg
*Attorney, Agent, or Firm*—Nawrocki, Rooney & Sivertson

[57] ABSTRACT

The present invention is a device and method for controlling longitudinal movement of a tube relative to a shaft slidably disposed within the tube, especially in the catheterization of a patient. An operative segment on the shaft cooperates with an ancillary tool to create a coupling force field between the shaft and the tool. The tube can then be moved over the shaft while the coupling force field operates through the tube to restrict the movement of the shaft. In the preferred embodiment, the shaft is a guide wire and the tube is a catheter with a lumen for slidably receiving the guide wire, while the coupling force field is created magnetically. In one embodiment, the operative segment is borne on a short guide wire extension which is selectively securable to a standard guide wire.

5 Claims, 21 Drawing Sheets

U.S. PATENT DOCUMENTS

| | | | |
|---|---|---|---|
| 4,726,369 | 2/1988 | Mar | 128/303 |
| 4,784,117 | 11/1988 | Miyazaki | 128/4 |
| 4,784,646 | 11/1988 | Feingold | 604/175 |
| 4,790,809 | 12/1988 | Kuntz | 604/8 |
| 4,804,054 | 2/1989 | Howson et al. | 604/48 |
| 4,809,713 | 3/1989 | Grayzel | 128/785 |
| 4,875,489 | 10/1989 | Messner et al. | 128/772 |
| 4,922,923 | 5/1990 | Gambale et al. | 128/772 |
| 5,020,367 | 6/1991 | White | 73/319 |
| 5,035,686 | 7/1991 | Crittenden et al. | 604/96 |
| 5,117,838 | 6/1992 | Palmer et al. | 128/772 |
| 5,156,594 | 10/1992 | Keith | 604/96 |
| 5,161,534 | 11/1992 | Berthiaume | 128/657 |
| 5,234,407 | 8/1993 | Teirstein et al. | 604/53 |
| 5,257,636 | 11/1993 | White | 128/897 |
| 5,269,759 | 12/1993 | Hernandez et al. | 604/96 |
| 5,464,023 | 11/1995 | Viera | 128/772 |

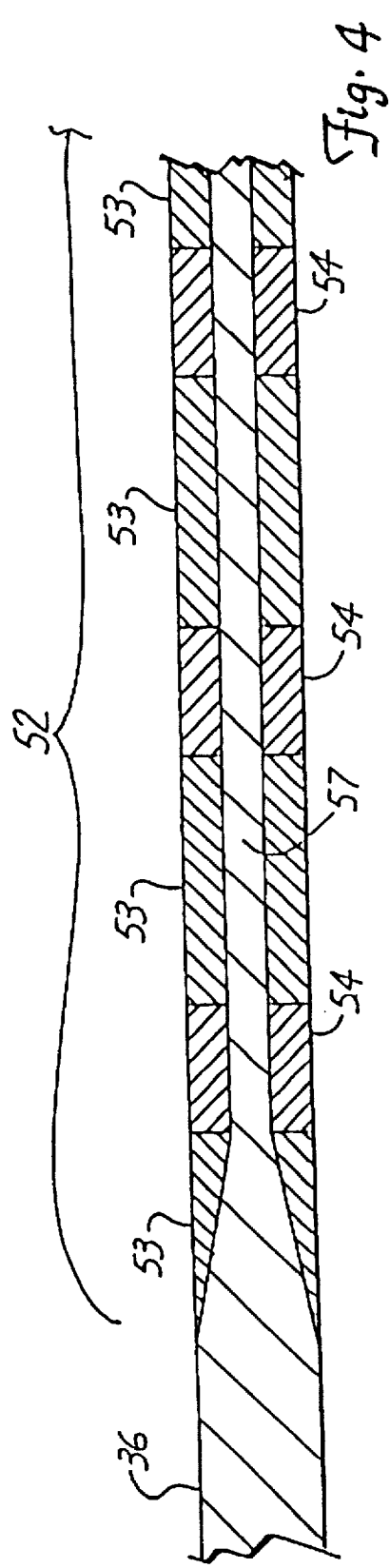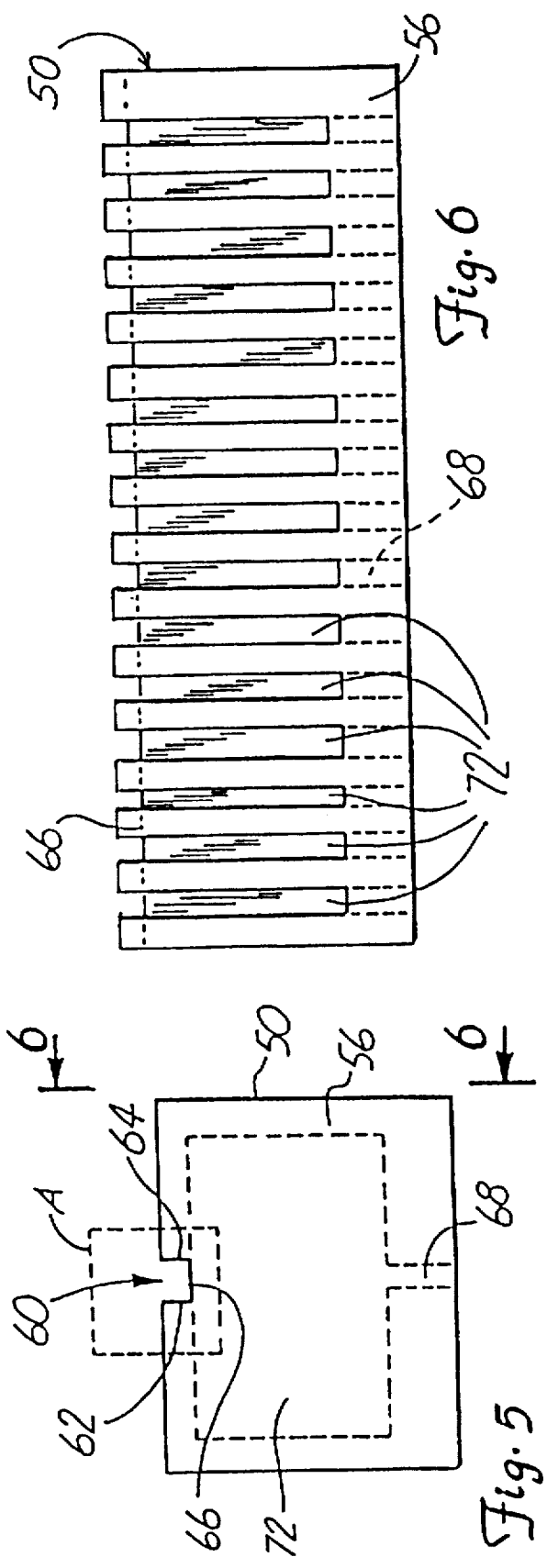

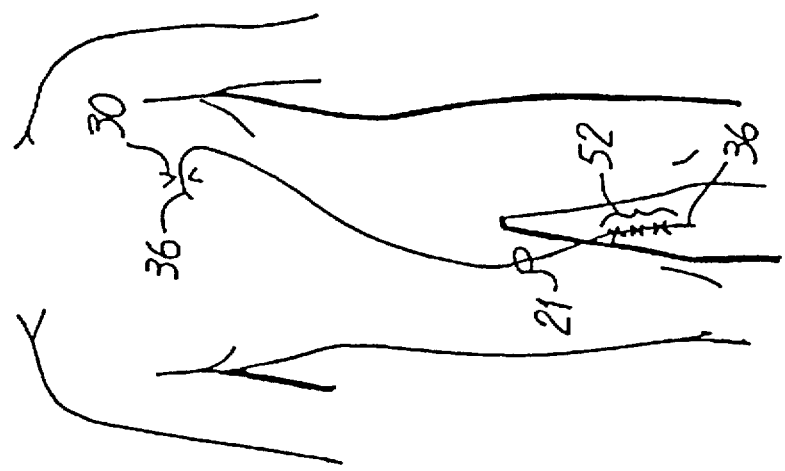
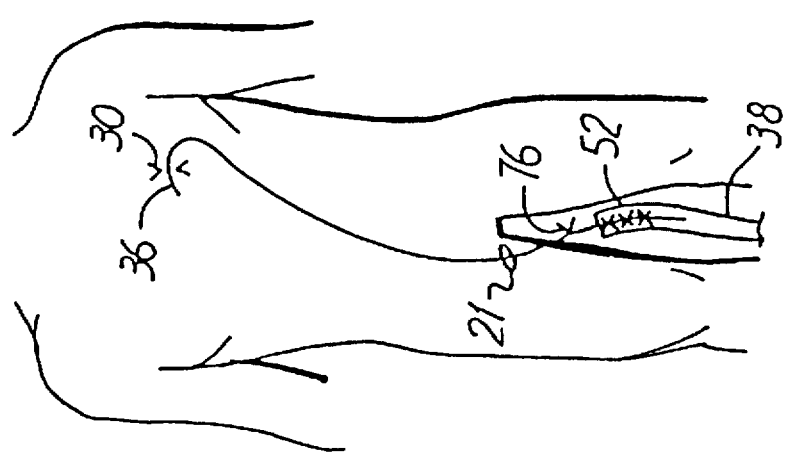

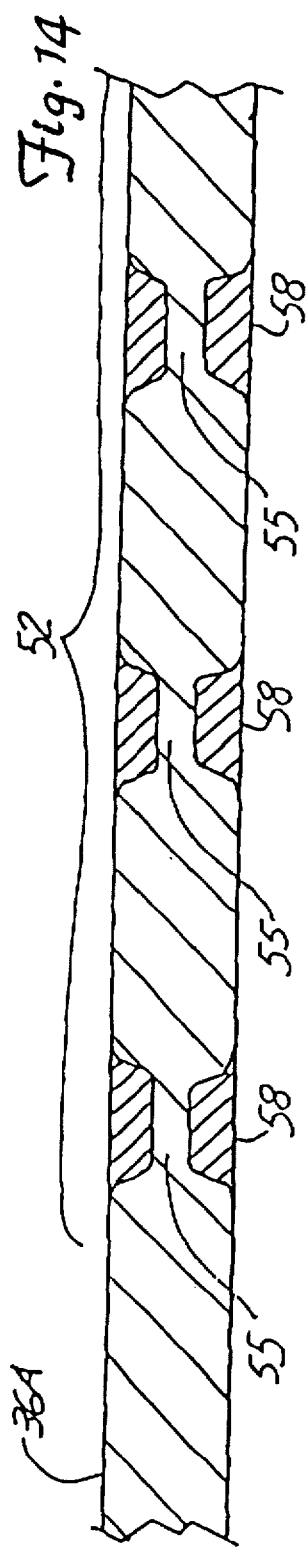
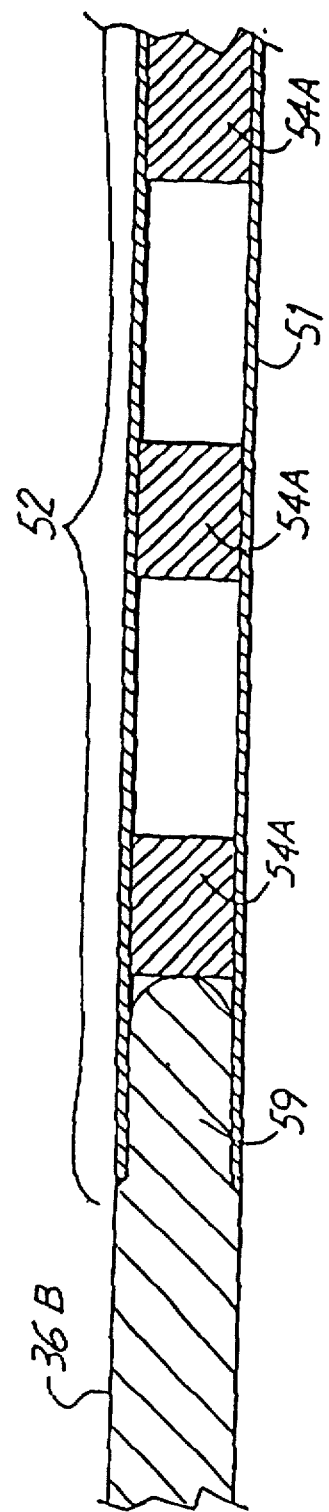

SHAFT MOVEMENT CONTROL APPARATUS

CROSS REFERENCES TO APPLICATIONS

This application is a continuation of application Ser. No. 08/369,190, filed Jan. 5, 1995, now abandoned, which in turn is a continuation-in-part application of application Ser. No. 08/048,492, filed Apr. 16, 1993, now U.S. Pat. No. 5,555,853, which in turn is a continuation-in-part of application Ser. No. 07/929,083, filed Aug. 12, 1992, now U.S. Pat. No. 5,623,943.

BACKGROUND OF THE INVENTION

The present invention relates to the field of medical devices, particularly catheters. In particular, the present invention relates to a method and device for controlling movement of an elongate shaft for use in the catheterization of a patient, where a portion of the shaft is inserted within the patient.

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the dilatation catheter through the vascular system until the balloon is positioned across the stenosis. The balloon is then inflated by supplying a fluid under pressure through an inflation lumen to the balloon. The inflation of the balloon causes stretching of the artery and pressing the lesion into the artery wall to re-establish acceptable blood flow through the artery. In some angioplasty procedures, it may be desirable to use a series of dilatation catheters having different sizes or balloon configurations.

One type of dilatation catheter has a guide lumen provided therein so that a guide wire can be used to establish the path through the stenosis. The dilatation catheter is then advanced over the guide wire until the balloon is positioned across the stenosis. The use of a guide wire enables the catheter to be advanced through the blood vessel relatively quickly, thereby reducing the time required for the procedure.

A "standard" guide wire for use in coronary angioplasty is about 175 cm long while a typical coronary angioplasty catheter is about 150 cm long. When the catheter is in place over the guide wire for use, a portion of the guide wire protrudes proximally from the catheter. The protruding portion enables the guide wire to be manipulated by a physician.

In some instances, it may be desirable to exchange one dilatation catheter (already on the guide wire) for a second dilatation catheter. It is usually preferred that the catheter be removed in a manner which enables the guide wire to remain in place in the blood vessel so that the succeeding catheter may be inserted into the blood vessel, over the guide wire already in place, and guided to the stenosis in the blood vessel. To maintain a guide wire in place while withdrawing the catheter, the guide wire must be gripped at its proximal end to prevent it from being pulled out of the blood vessel with the catheter. The catheter, however, is longer than the proximal portion of the guide wire which protrudes out the patient. Thus, before the catheter is fully withdrawn, it completely covers the proximally extending portion of the guide wire. As a result, there was no means by which a standard guide wire can be held in place to prevent it from being withdrawn together with the catheter. To withdraw the catheter while leaving the guide wire in place, a guide wire with a longer effective length was required.

One means for addressing this difficulty is to use an exchange wire when performing a catheter exchange. An exchange wire may be used initially or may be exchanged for a standard guide wire already in place in the patient. An exchange wire typically is much longer (e.g., 300 cm) than the typical or standard guide wire. The additional length of the exchange wire results in a proximally protruding portion which is longer than the length of the catheter to be removed. When a catheter is removed, some part of the proximally protruding portion of the exchange wire is always exposed to provide a means by which the exchange wire can be gripped and its position in the blood vessel maintained. The succeeding catheter is then inserted into the patient over the exchange wire.

It is generally recognized as undesirable to insert, advance and withdraw a series of guide wires during these types of procedures. Repeated guide wire insertions increase the risk of injury to the patient and also increase the time required for the procedure. It also requires exposure of the patient to additional radiation because of the additional fluoroscopy which is required to properly place the successive guide wires across the stenosis. In addition, long exchange wires are cumbersome and difficult to handle while maintaining the guide wire in place across the stenosis.

Techniques to eliminate the need to change guide wires have been proposed. One solution is the use of a guide wire extension which is attached to the proximal end of the guide wire while the guide wire remains in place in the patient. The guide wire extension effectively increases the length of the guide wire to that of an exchange guide wire. While the technique substantially shortens the duration of the procedure because the extension can be attached at the proximal end of the guide wire much faster than an exchange of guide wires can be performed, the extended guide wire is still cumbersome as the physician is required to handle an extended length of a guide wire outside of the patient during at least a portion of the procedure.

One means for catheter exchange without lengthening the guide wire is by use of a balloon catheter with a guide wire lumen located only adjacent the distal end of the catheter. With this configuration, the guide wire is external to the balloon catheter except adjacent the distal end of the balloon catheter. This catheter arrangement allows the catheter to be withdrawn over the guide wire without requiring the physician to completely release the guide wire until the distal end of the catheter is outside of the patient's body. The guide wire lumen on the catheter is shorter than the length of exposed guide wire, which allows at least some portion of the proximal end of the guide wire to be exposed at all times so that it can be grasped and its position relative to the stenosis can be maintained during removal of the catheter.

Another means for exchanging a catheter without the use of an extended guide wire is to engage the guide wire at a point distally of the catheter and hold it in place relative to the stenosis. This has been done by providing an inflatable guide wire holding balloon which is adapted to be inflated only within a guide catheter. In this arrangement, the dilatation catheter in the patient is withdrawn over the guide wire and inside of the guide catheter a short distance. The guide wire holding balloon is aligned distally relative to the dilatation catheter and is then inflated, thereby "trapping"

the guide wire against an inner wall of the guide catheter (and constraining the guide wire from longitudinal movement relative to the guide catheter). The dilatation catheter is then withdrawn over the guide wire (the proximal end of the guide wire can be released) and a second dilatation catheter is placed on the guide wire and advanced along the guide wire to the point where the guide wire is trapped against the guide catheter wall. The guide wire holding balloon is then deflated and the physician advances the second dilatation catheter along the guide wire to the stenosis to continue the procedure. It also has been disclosed that mechanical means such as a wire snare be used within a guide catheter to secure the guide wire thereto, instead of a balloon.

While arrangements have been proposed to facilitate catheter exchanges in guide wire catheter systems without the need for a long guide wire length, they require a modified catheter (no full-length guide wire lumen) or additional components within the patient (e.g., balloon for trapping guide wire within guide catheter). It is desired to devise an arrangement which allows catheter exchanges over a standard length guide wire using a catheter having a full-length guide wire lumen.

SUMMARY OF THE INVENTION

The present invention is a method and device for controlling movement of a shaft for use in the catheterization of a patient where a distal portion of the shaft is inserted within the patient. The present invention is also useful for facilitating movement of a tube relative to a shaft extending through the tube, where distal portions of both the tube and the shaft are inserted within a patient.

The device of the present invention includes two pieces used in conjunction with each other. The first piece is an operative segment on the shaft. The second piece is an ancillary tool which, when positioned adjacent the operative segment on the shaft, cooperates with the operative segment to create a coupling force field between the operative segment and the tool, thus coupling the tool and the shaft together. The force created between the two pieces is strong enough to maintain the position of the shaft relative to the tool when the tube is aligned over the operative segment of the shaft.

In one preferred embodiment, the present invention is used to facilitate catheter exchanges in a guide wire catheter system without the need for a long guide wire length. In this preferred embodiment, the shaft is a guide wire, and the tube is a catheter with a lumen for slidably receiving the guide wire. The coupling force field between the operative segment on the guide wire and the tool is created by magnetism and is strong enough to maintain the tool and the guide wire in a coupled relation when the catheter is aligned over the operative segment on the guide wire and the catheter is moved longitudinally relative to the guide wire. The materials used to create the magnetic coupling force may be permanent magnets or magnetically permeable material.

The present invention is ideally suited for facilitating catheter exchanges without the need for a long guide wire length or a modified catheter. When a guide wire catheter system utilizing the present invention is pre-inserted within the vessel of a patient, the original catheter may be exchanged for a second catheter by simply aligning the operative segment on the guide wire with the tool to create the coupling force field; withdrawing the original catheter proximally past the tool and over the guide wire (which is held stationary relative to the tool) until the catheter is free of the guide wire; aligning the second catheter over the guide wire; and advancing the second catheter past the tool and over the guide wire until the second catheter is properly positioned. A handle, which couples fixedly to the tool and slidably to the catheter assembly, provides for ease of operation. The catheter assembly is stabilized within the tool through the use of a geometrically configured catheter receiving notch.

BRIEF DESCRIPTION OF THE DRAWINGS

The invention will be further described with reference to the accompanying drawings where like numbers refer to like parts in several views and wherein:

FIG. 4 is a detail sectional view of an operative segment of a guide wire which is one preferred embodiment of the present invention.

FIG. 5 is a view in end elevation showing one preferred embodiment of the present invention.

FIG. 6 is a view in side elevation along line 6—6 in FIG. 5.

FIGS. 8–13 depict a preferred method of use for the present invention.

FIG. 8 shows the catheter and guide wire pre-inserted in a vessel of a patient, with the operative segment on the guide wire disposed within the proximal end of the dilatation catheter.

FIG. 9 shows the tool being placed over the operative segment of the guide wire.

FIG. 10 shows the dilatation catheter being withdrawn over the guide wire and past the tool.

FIG. 11 shows the dilatation catheter external from the patient's body with the tool adjacent the operative segment on the guide wire.

FIG. 12 shows the dilatation catheter external to the patient's body with the tool removed from adjacent the guide wire.

FIG. 13 shows the guide wire remaining in place in the vessel of the patient with the tool and dilatation catheter removed.

FIG. 14 is a detail sectional view of an operative segment of a guide wire which is another preferred embodiment of the present invention.

FIG. 15 is a detail sectional view of an operative segment of a guide wire which is another preferred embodiment of the present invention.

While the above identified drawing features set forth preferred embodiments, other embodiments of the present invention are also contemplated, as noted in the discussion. This disclosure presents illustrative embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity.

DETAILED DESCRIPTION OF THE PREFERRED EMBODIMENTS

The present invention is a method and device for controlling movement of an elongated shaft in the catheterization of a patient, where a portion of the shaft is inserted within the patient. More precisely, the present invention is a method and device for controlling the movement of an elongated shaft extending through an elongated tube, wherein a portion of both the tube and shaft are inserted within the patient. In one preferred embodiment, the shaft is a guide wire and the tube is a catheter with a lumen for slidably receiving the guide wire.

Figure 1:
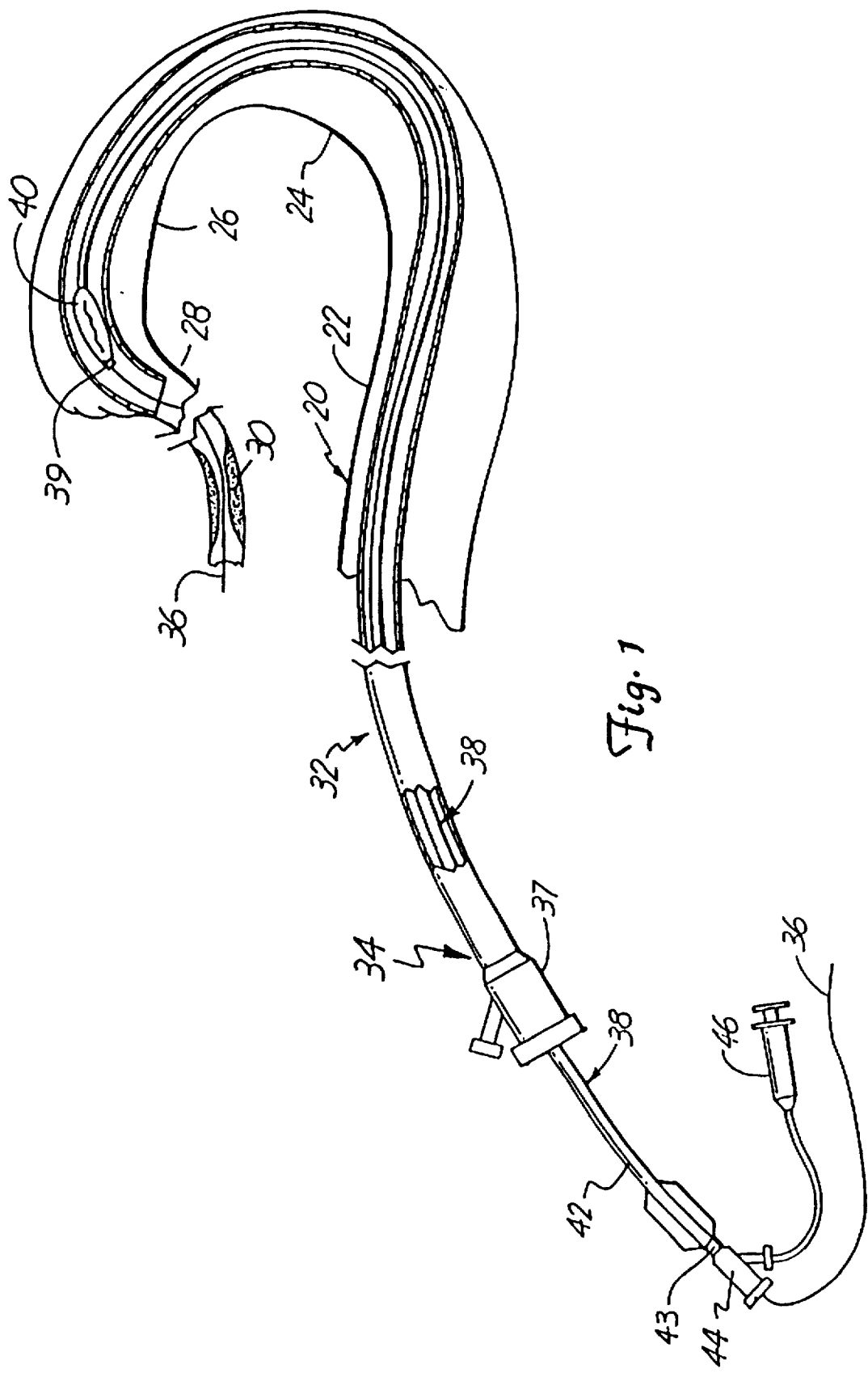
FIG. 1 is a diagrammatic view of an angioplasty catheter system in the vascular system of a patient.

A vascular system 20 and an angioplasty catheter system 32 are shown in FIG. 1. In an angioplasty procedure, entry into the vascular system 20 is typically through the femoral artery in the thigh (as schematically shown at 21 in FIGS. 2 and 8). A distal portion of the vascular system 20 includes a descending aorta 22, an aortic arch 24, and an ascending aorta 26. Extending from the ascending aorta 26 is a coronary artery 28, in which a stenosis 30 is formed.

The angioplasty catheter system 32 includes a guide catheter 34, a guide wire 36 extending through the guide catheter 34, and a dilatation catheter 38 with an inflatable balloon 40 mounted at a distal end 39 of a main tubular shaft 42 of the dilatation catheter 38. The dilatation catheter 38 is designed for use in conjunction with a guide wire, and has a guide wire lumen 45 (FIGS. 2, 3 and 7) extending along its entire length. The dilatation catheter 38 also has an inflation lumen 47 extending therethrough. The dilatation catheter 38 may be a dual lumen or coaxial lumen structure. In a coaxial arrangement (as shown), the inflation lumen 47 is provided between the outer main shaft 42 and an inner tubular shaft 41 disposed coaxially within the outer shaft 42. The guide wire lumen 45 is thus defined by the interior of the inner tubular shaft 41.

As illustrated in FIG. 1, a proximal portion of the guide wire 36 protrudes proximally out of a proximal end 43 of the dilatation catheter 38 and a proximal portion of the dilatation catheter 38 protrudes proximally out of a Y-adaptor 37 connected to a proximal end of the guide catheter 34. An inflation manifold 44 is connected to the proximal end 43 of the dilatation catheter 38 for facilitating inflation of the balloon 40. An inflation device 46 for inflating the balloon 40 is in fluid communication with the balloon 40 via the inflation manifold 44 and the inflation lumen 47.

The basic angioplasty procedure consists of inserting the guide catheter 34 into the vascular system 20 at the femoral artery. The guide catheter 34 is advanced through the vascular system 20 until a distal end of the guide catheter 34 is adjacent the mouth of the coronary artery 28 as shown in FIG. 1. Next, the distal end 39 of the dilatation catheter 38 is loaded onto and over a proximal end of the guide wire 36 and advanced over the guide wire 36 until the distal end 39 of the dilatation catheter 38 is adjacent a distal end of the guide wire 36. Then, the assembled combination of the guide wire 36 and the dilatation catheter 38 is inserted into the proximal end of the guide catheter 34 and advanced distally therethrough, retracing the already established path of the guide catheter 34 through the patient's vascular system 20. The guide wire 36 and the dilatation catheter 38 combination typically is advanced distally until adjacent the distal end of the guide catheter 34. The distal tip of the guide wire 36 is then advanced separately and manipulated into the artery tree to and across the stenosed artery. The dilatation catheter 38 is then advanced over the guide wire 36 to position the balloon 40 across the stenosis 30. The balloon 40 is inflated to dilate the stenosis 30 to re-establish acceptable blood flow through the artery.

However, sometimes the dilatation catheter 38 must be exchanged for another dilatation catheter to complete the angioplasty procedure. When exchanging the dilatation catheter 38 for another catheter, it is desirable to hold the guide wire 36 in place across the stenosis 30 during withdrawal of the dilatation catheter 38 (and advancement of the next catheter) to eliminate the need to re-establish the position of the guide wire 36 by retracing the tortuous path to the stenosis 30 after the dilatation catheter 38 is exchanged. Maintaining the guide wire 36 in place after an initial dilatation also provides the physician with a path through the stenosis 30 in case of an abrupt closure of the vessel.

Figure 2:
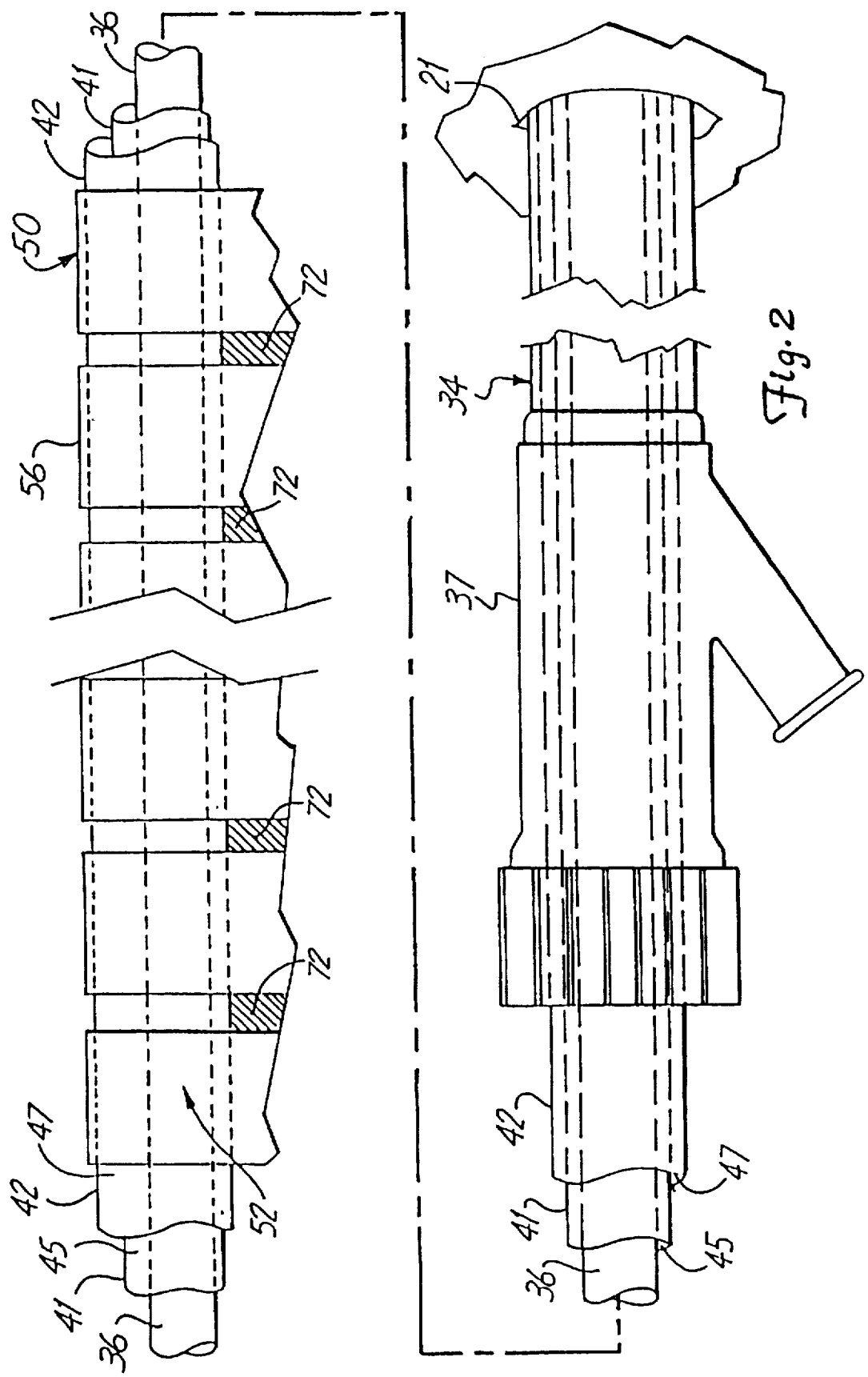
FIG. 2 is an enlarged view in side elevation of one embodiment of the present invention which shows guide wire captivation.

The present invention facilitates holding the guide wire 36 in place across the stenosis 30 without requiring an exchange wire, an extension wire or additional intravascular devices to accomplish the dilatation catheter exchange over the guide wire 36. In one form of the present invention, means are provided proximally of the guide catheter Y-adaptor 37 to cooperate with the guide wire 36 for maintaining the position of the guide wire 36 across the stenosis 30. One preferred embodiment of the present invention, as shown in FIGS. 2–7, employs a captivation tool 50 which cooperates with an operative segment 52 of the guide wire 36 to create a coupling force field between the tool 50 and the operative segment 52. The coupling force field is defined by an energy field (such as a magnetic field). The force generated by the field is strong enough to maintain the position of the guide wire 36 relative to the tool 50 when the dilatation catheter 38 is aligned over the operative segment 52 of the guide wire 36, and particularly when the dilatation catheter 38 is moved over the guide wire 36. As shown in FIG. 2, the operative segment 52 of the guide wire 36 is located on a proximal portion of the guide wire 36 and is positioned so that the operative segment 52 is located some distance beyond the proximal end of the guide catheter Y-adaptor 37.

Figure 3:
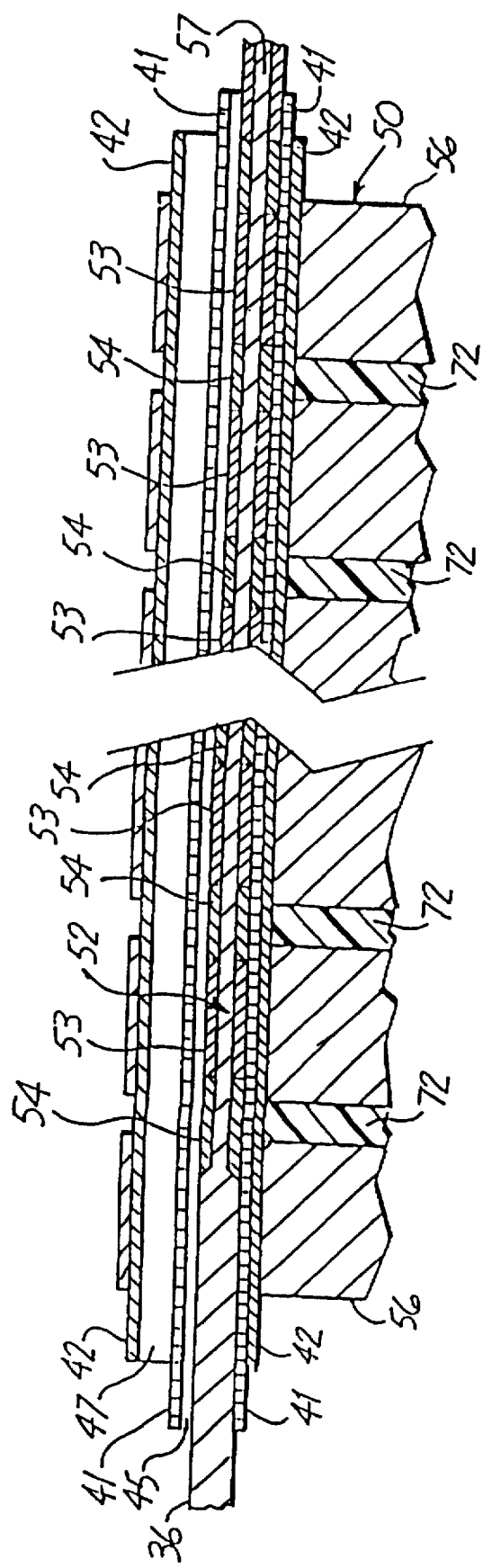
FIG. 3 is a sectional view of the captivation tool in FIG. 2.

As seen in FIG. 3, the operative segment 52 of the guide wire 36 includes a plurality of magnetically permeable segments 54 secured on the guide wire 36 at locations along the guide wire 36. (Examples of suitable magnetically permeable materials are Rodar, manufactured by T. N. Wilbur B. Driver Company and available in tube form from Uniform Tubes of Collegeville, Pa.; Hiperco Alloy 50, manufactured by Carpenter Steel of Reading, Pa.; Permendur or 2V Permendur, listed as high permeable magnetic materials having large saturation flux densities in the CRC Handbook of Chemistry and Physics, 47th ed.; or any other material with a suitably large residual induction). In this embodiment, as seen in FIGS. 3 and 4, the operative segment 52 includes a plurality of magnetically permeable segments 54 secured about a reduced diameter portion 57 of guide wire 36. Non-magnetically permeable segments 53 are disposed between and about each of the magnetically permeable segments 54, respectively. In all embodiments of the operative segment 52 on the guide wire 36, the outside diameter of the operative segment 52 stays essentially the same as the outside diameter of the guide wire 36, and the transitions between magnetically permeable and non-magnetically permeable materials are smooth and distinct.

Figure 7:
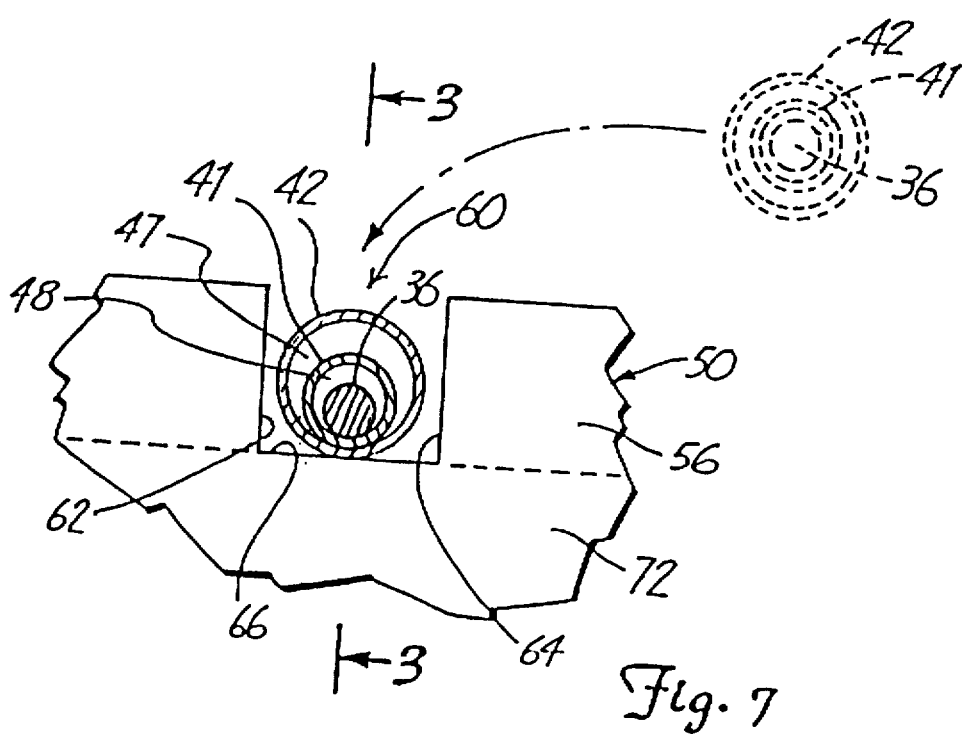
FIG. 7 is an enlarged fragmentary detail of portion A in FIG. 5 illustrating the placement of a catheter assembly, shown in section, into the tool housing.

As seen in FIGS. 5–7, the captivation tool 50 includes a housing member 56. The housing member 56 includes a longitudinal slot 60 defined by a pair of side slot surfaces 62 and 64, and a bottom slot surface 66. The slot 60 provides a space with sufficient size to slidably receive the dilatation catheter 38 and allow the dilatation catheter 38 to longitudinally pass freely through the slot 60, yet still restrict lateral movement of the dilatation catheter 38 between the slot surfaces 62, 64, and 66.

The housing member 56 also includes a plurality of rectangular-shaped magnetic sections 72 (shown in phantom in FIG. 5) which have exposed surfaces at bottom slot surface 66. As best seen in FIG. 6, the magnetic sections 72 are provided at longitudinally spaced locations along the housing member 56 corresponding to the spacing of the magnetically permeable sections 54 on the guide wire 36. The magnetically permeable sections 54 on the guide wire 36 and the magnetic sections 72 in the housing member 56 are spaced such that they can be aligned across from each other as shown in FIG. 3. Although the material of the bottom slot surface 66 alternates between the housing member 56 and the magnetic sections 72, the bottom slot surface 66 is smooth. The magnetic sections 72 are preferably made from a strong magnetic material with a large cohesive force (such as neodynium boron iron) that can hold a magnetization through a relatively thin section.

The size and spacing of the magnetic sections 72, as well as the size and spacing of the magnetically permeable sections 54 of the operative segment 52 on the guide wire 36, are chosen to maximize the longitudinal attractive force on the guide wire 36 while minimizing the radial attractive force on the guide wire 36. The net force for maintaining the position of the guide wire 36 relative to the tool 50 is governed by the equation:

$$F_{net} = F_L - \mu F_R$$

where $F_{net}$ is the net force available to maintain the position of the guide wire 36, $F_L$ is the longitudinal force of attraction between the tool 50 and the operative segment 52 on the guide wire 36, $F_R$ is the radial force of attraction between the tool 50 and the operative segment 52, and $\mu$ is the friction coefficient between the guide wire 36 and the dilatation catheter 38.

Thus, to obtain optimum performance from the device, it is desirable to maximize the force $F_L$ and minimize the force $F_R$ and the friction coefficient $\mu$. The friction coefficient $\mu$ may be reduced through the use of lubricous coatings and materials, and the attractive forces $F_L$ and $F_R$ may be optimized through the use of mathematical modeling techniques known in the art. For example, positioning the magnetic sections 72 in the tool 50 such that the polarity of the magnetic sections 72 alternates between magnetic sections 72 reduces the radial attractive force $F_R$. Such alternation increases the total effective magnetic field, thereby increasing the longitudinal holding force. The total coupling force between the operative segment 52 and the tool 50 is proportional to the number of magnetic sections 72 in the tool 50.

In one preferred embodiment, the guide wire 36 has an outside diameter of 0.018 inches. The operative segment 52 has a length of approximately 10 inches with approximately 50 magnetically permeable sections 54, each having a length of 0.1 inch, separated by non-magnetically permeable sections 53 with a length of 0.1 inch. A non-operative segment approximately 2 inches long is attached to the proximal end of the operative segment 52. The tool 50 is approximately 4.0 inches long, 1.0 inch high, and 1.0 inch wide, with 20 magnetic sections (magnets) 72 spaced 0.2 inches apart. The magnetic sections 72 are 0.04 inches thick and 0.75 inches high, with a width of 0.75 inches. The height and width of the magnetic sections 72 are determined as a function of the thickness of the magnetic sections 72. The magnetic poles of the magnetic sections 72 are alternated so that like poles of the spaced magnetic sections 72 are facing each other. The slot 60 for receiving the dilatation catheter 38 is 0.10 inch wide and 0.10 inch deep. The holes 68 centered under each of the magnetic sections 72 (for gluing magnetic sections 72 in place during assembly) are approximately 0.04 inches in diameter.

Figure 9:
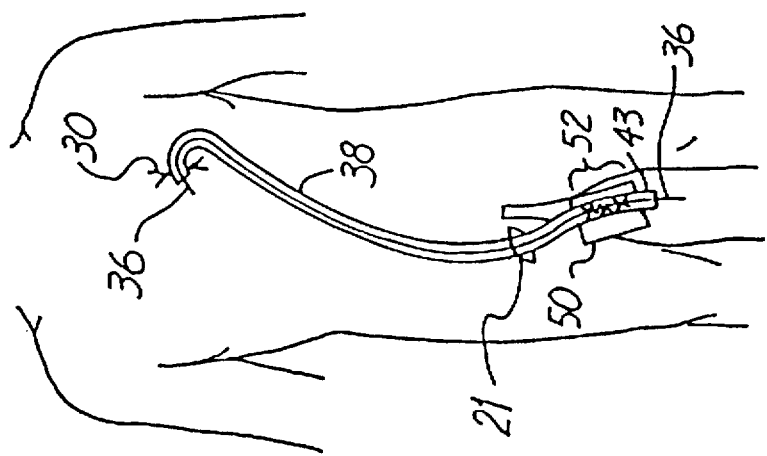
Figure 8:
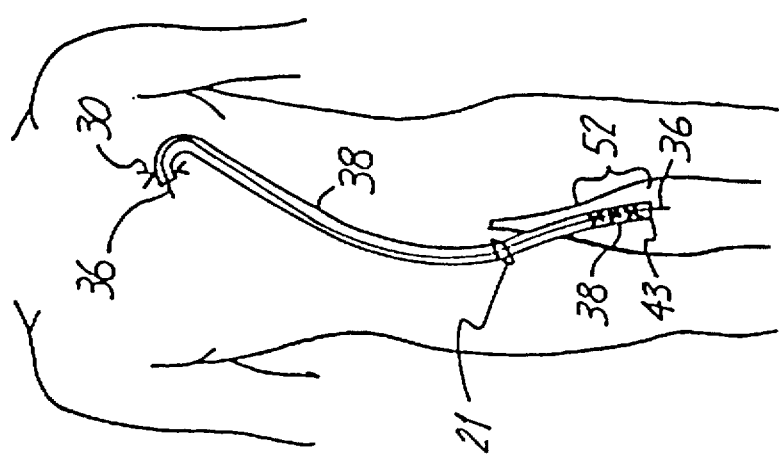

The device of the present invention for facilitating a dilatation catheter exchange while maintaining a guide wire in place within a vessel is employed in the following manner. Of course, performing such an exchange requires that the angioplasty catheter system 32 already be in place in the vascular system 20 of the patient as previously described. As such, the proximal end of the guide wire 36 and the proximal end 43 of the dilatation catheter 38 protrude proximally outside the patient as seen in FIG. 8, with the proximal end of the guide wire 36 extending proximally beyond the proximal end 43 of the dilatation catheter 38. Recall that the operative segment 52 of the guide wire 36 (identified schematically by the "xxx's" in FIGS. 8–13) is located near the proximal portion of the guide wire 36 and is disposed within the proximal end 43 of dilatation catheter 38. To begin the exchange, the physician grasps the proximal end of the guide wire 36 to maintain its distal end in place across the stenosis 30. The physician then places a proximal portion of the dilatation catheter 38 (having the operative segment 52 extending therein) into the slot 60 of the housing member 56 (see FIGS. 7 and 9) and aligns the operative segment 52 with the tool 50.

The alignment of the operative segment 52 with the tool 50 is relatively simple because the operative segment 52 is longer than the slot 60 in the tool 50, and the distance between the magnetically permeable sections 54 on the guide wire 36 and the corresponding magnetic sections 72 on the tool 50 is relatively small. The result is that when the operative segment 52 is positioned within the slot 60 of the tool 50 only a small amount of movement (less than half the distance between the magnetic sections 72 on the tool 50) is required to align the magnetically active portions of the operative segment 52 and the tool 50. As the spacing between the magnetic sections 72 becomes smaller, less movement is required to align the tool 50 and the operative segment 50. At the given dimensions, the tool 50 and the operative segment 52 effectively become self-aligning, and simply positioning the operative segment 52 within the slot 60 of the tool 50 ensures proper alignment.

Once the operative segment 52 on the guide wire 36 is properly aligned with the magnetic sections 72 of the captivation tool 50, the guide wire 36 is attracted to the captivation tool 50 by the resultant magnetic field created therebetween (see FIGS. 2, 3, and 7). This results in the guide wire 36 being pulled (along with the dilatation catheter shafts 41 and 42) against the bottom slot surface 66 of the housing member 56 as seen in FIGS. 3 and 7. The drawings are exaggerated for clarity in this regard.

Once the guide wire and tool 50 have been so coupled, the physician releases the guide wire 36 proximal to the tool 50 and then grasps the proximal end 43 of the dilatation catheter 38 proximally of the tool 50. The dilatation catheter 38 is pulled proximally over the guide wire 36 and past the tool 50 while holding the tool 50 (and thus the guide wire 36) in a stationary position relative to the patient (see FIG. 10). The physician may choose to hold the tool 50 in his hand, or alternately the physician may place the tool 50 on the table to hold the tool 50 stationary. The longitudinal magnetic attraction between the guide wire 36 and the captivation tool 50 is greater than the friction between the guide wire 36 and the inner catheter shaft 41. Accordingly, the dilatation catheter 38 may be pulled over the guide wire 36 while maintaining the guide wire 36 in the same position relative to the captivation tool 50. This ultimately maintains the guide wire 36 in position across the stenosis 30 during this maneuver, as long as the tool 50 is held generally stationary with respect to the patient.

Figure 11:
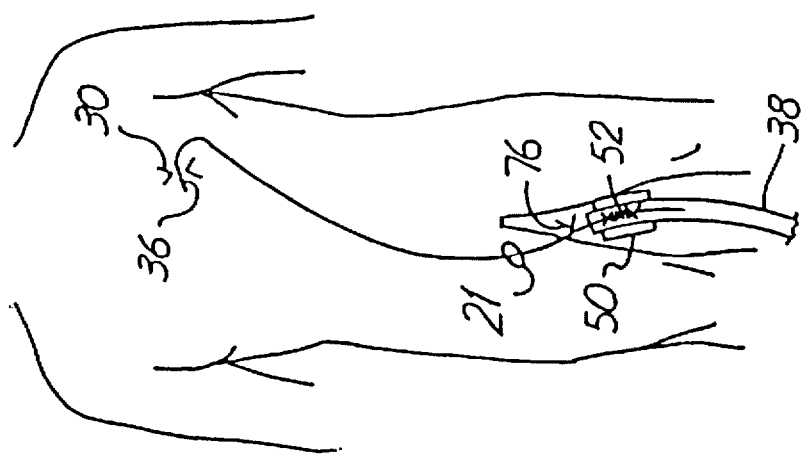
Figure 10:
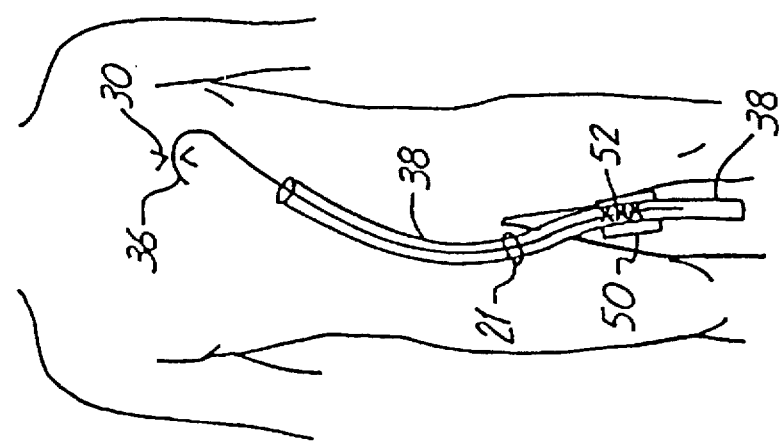

The catheter 38 is withdrawn until the distal end of the dilatation catheter 38 is exposed outside of the patient's body as seen in FIG. 11. As such, a portion of the guide wire 36 will be exposed between the distal end of the catheter 38 and the proximal end of the guide catheter 34, which protrudes outside the patient's body. The physician then grasps this exposed portion of the guide wire 36 distal to the tool 50 and the distal end of the dilatation catheter 38 as at 76. The physician then laterally separates the catheter 38 and the guide wire 36 therein from the tool 50 by overcoming the radial magnetic forces between the guide wire operative segment 52 and the tool 50. The physician then completely withdraws the first balloon catheter 38 proximally off of the guide wire 36. The guide wire 36 has thus been held in a generally stationary position during the entire catheter removal procedure in a very simple and elegant manner, which can be managed by the physician without the need for extra persons to hold or manipulate additional catheter or guide wire components.

Next, while still maintaining the guide wire 36 in place by grasping at 76, a second dilatation catheter is placed on the proximal end of the guide wire 36 and moved distally over the guide wire 36 until the operative segment 52 of the guide wire 36 is positioned within a distal end of the second dilatation catheter (preferably within the second catheter at a point proximal to the balloon thereon). The operative segment 52 of the guide wire 36 and the tool 50 are positioned together (as previously described) until the operative segment 52 is magnetically aligned with the magnetic sections 72 of the captivation tool 50. The physician then releases the guide wire 36 distally of the tool 50 as at 76, grasps the second dilatation catheter, and distally advances the second dilatation catheter over the guide wire 36 longitudinally relative to tool 50 and the guide wire 36 to distally advance the second catheter through the guide catheter 34. During dilatation catheter advancement, the captivation tool 50 is held stationary relative to the patient to ultimately maintain the distal end of the guide wire 36 in place across the stenosis 30. The second dilatation catheter is advanced distally over the guide wire 36 until the proximal end of the guide wire 36 extends beyond a proximal end of the second dilatation catheter. The physician then grasps the guide wire 36 proximal to the tool 50 and dilatation catheter manifold 44, and separates the second dilatation catheter and the guide wire 36 therein from the tool 50. The second dilatation catheter is then further advanced distally over the guide wire 36 until the balloon of the second dilatation catheter is across the stenosis 30 for dilatation. The dilatation catheter exchange procedure using the captivation tool 50 and operative segment 52 can thus be repeated in this manner as necessary.

During the dilatation catheter removal and insertion procedure, the position of the guide wire 36 is maintained relative to the guide catheter 34, and more importantly, relative to the stenosis 30. The present invention is ideally suited for facilitating catheter exchanges without the need for a long exchange guide wire, a modified catheter, or additional intravascular devices such as a guide wire holding balloon for "trapping" the guide wire against a wall of the guide catheter. The present invention allows catheter exchanges over a standard length guide wire using a catheter having a full length guide wire lumen. Additionally, the procedure may be performed by a single physician and without the prolonged use of X-ray fluoroscopy used to observe the position of the guide wire, since the guide wire is held stationary by use of the present invention and thus its position need not be continuously observed.

The utility of the present invention is not limited to catheter exchange procedures. The present invention may be used as a "third hand" during a catheterization procedure. Typically during a catheterization procedure, the physician is required to simultaneously manipulate the guide wire 36, the dilatation catheter 38, and the guide catheter 34. The simultaneous manipulation often requires the use of additional medical personnel, which increases the cost and complexity of the procedure. By placing the operative segment 52 adjacent the tool 50 and securing the tool 50 itself in a stationary position, the present invention eliminates the need for the physician (or a second person) to continually hold the guide wire 36 during the procedure. The operative segment 52 provided on the guide wire 36 can be made long enough to allow the use of more than one tool 50 during a catheterization procedure. For example, when the physician is withdrawing the dilatation catheter 38 from the patient and is required to grasp the guide wire 36 before completely removing the dilatation catheter 38 from the guide wire 36 (e.g., when the physician grasps the guide wire 36 at 76 before completely withdrawing the dilatation catheter 38 of the guide wire 36, as seen in FIGS. 11 and 12 and as previously described), a second tool 50 may be used in place of the physician actually grasping the guide wire 36.

In alternate embodiments, the operative segment 52 on the guide wire 36 may take a number of forms including those shown in FIGS. 14, 15 and 21–28. In FIG. 14, each of a plurality of non-magnetically permeable segments 58 are secured about reduced diameter portions 55 of the guide wire 36A. The guide wire 36A is made of a magnetically permeable material, and segments 58 are a non-magnetically permeable material such as plastics or non-magnetic metals. As seen in FIG. 15, the operative segment 52 may include an elongate non-magnetically permeable tubular member 51 with a plurality of solid cylindrically-shaped magnetically permeable segments 54A secured within member 51. The tubular member 51 is connected to a reduced diameter portion 59 of the guide wire 36. Another embodiment of the operative segment 52 is a guide wire segment made of a single material which can exist in either a magnetic or non-magnetic state (such as martensite of austenite steel) depending upon the heat treatment of the material. Alternating sections of the wire are heat treated locally to form alternating magnetic and non-magnetic sections on the guide wire. In each embodiment of the operative segment 52, the magnetically permeable material may be replaced with permanent magnets.

Figure 16:
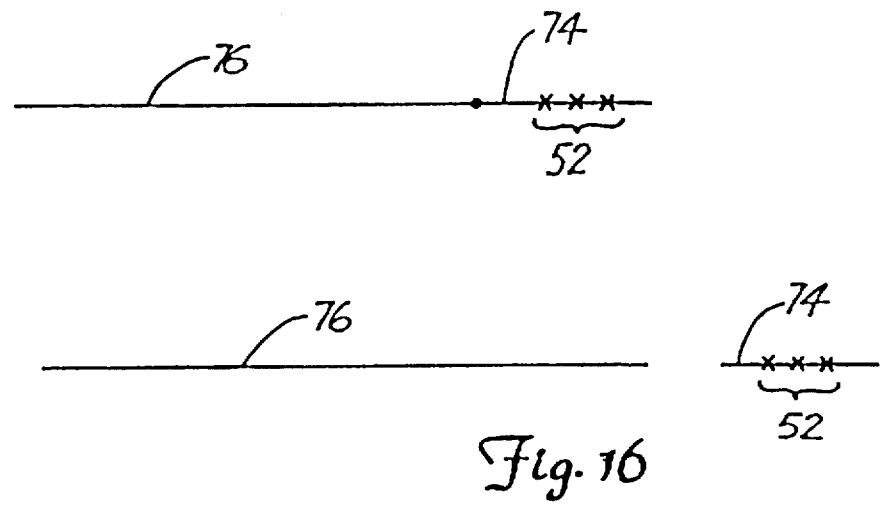
FIG. 16 is a schematic illustration of a guide wire extension containing an operative segment.

The operative segment 52 may be provided on a short guide wire extension 74 (e.g., about 12 inches long) for a standard guide wire. As shown schematically in FIG. 16, this short extension 74 would connect to the proximal end of the standard guide wire 76 in a conventional manner, such as shown, e.g., in U.S. Pat. Gambale et al. Nos. 4,922,923; Messner et al. 4,875,489; Crittenden et al. 5,035,686; or Palmer et al. 5,117,838. The short extension 74 is selectively attachable to the standard guide wire 76 and can be connected and disconnected multiple times during a single procedure. Use of the short guide wire extension 74 with an operative segment 52 allows the physician to perform a catheter exchange using the present invention even if the catheterization procedure was started using a standard guide wire 76. The use of the short extension 74 in a catheter exchange merely requires the additional acts of attaching the extension 74 to the guide wire 76 and withdrawing the original catheter proximally far enough to cover the operative segment 52 on the short extension 74 before positioning the dilatation catheter 38 relative to the tool 50 for magnetic coupling of the extended guide wire and the tool 50. Otherwise, the use of such a short guide wire extension 74, either for holding the wire/catheter assembly during the procedure or to facilitate a catheter exchange over a stationary wire, is essentially the same as described herein.

The tool 50 may be adapted to fit over the guide catheter 34 (as in a 2-piece "clam shell" design), may be made in the form of a guide catheter extension, or may be incorporated directly into the guide catheter Y-adaptor 37, for example. Additionally, the tool 50 may be designed such that the magnetic sections 72 in the tool 50 are moved within the housing member 57 and away from the slot 60 in the housing member 56. With this feature, the attraction between the tool 50 and the operative segment 52 on the guide wire 36 is effectively "turned off" when the magnetic sections 72 are moved sufficiently laterally away from the slot 60 in the housing member 56 and the operative segment 52 of the guide wire 36 therein to break the magnetic attraction therebetween.

Figure 18:
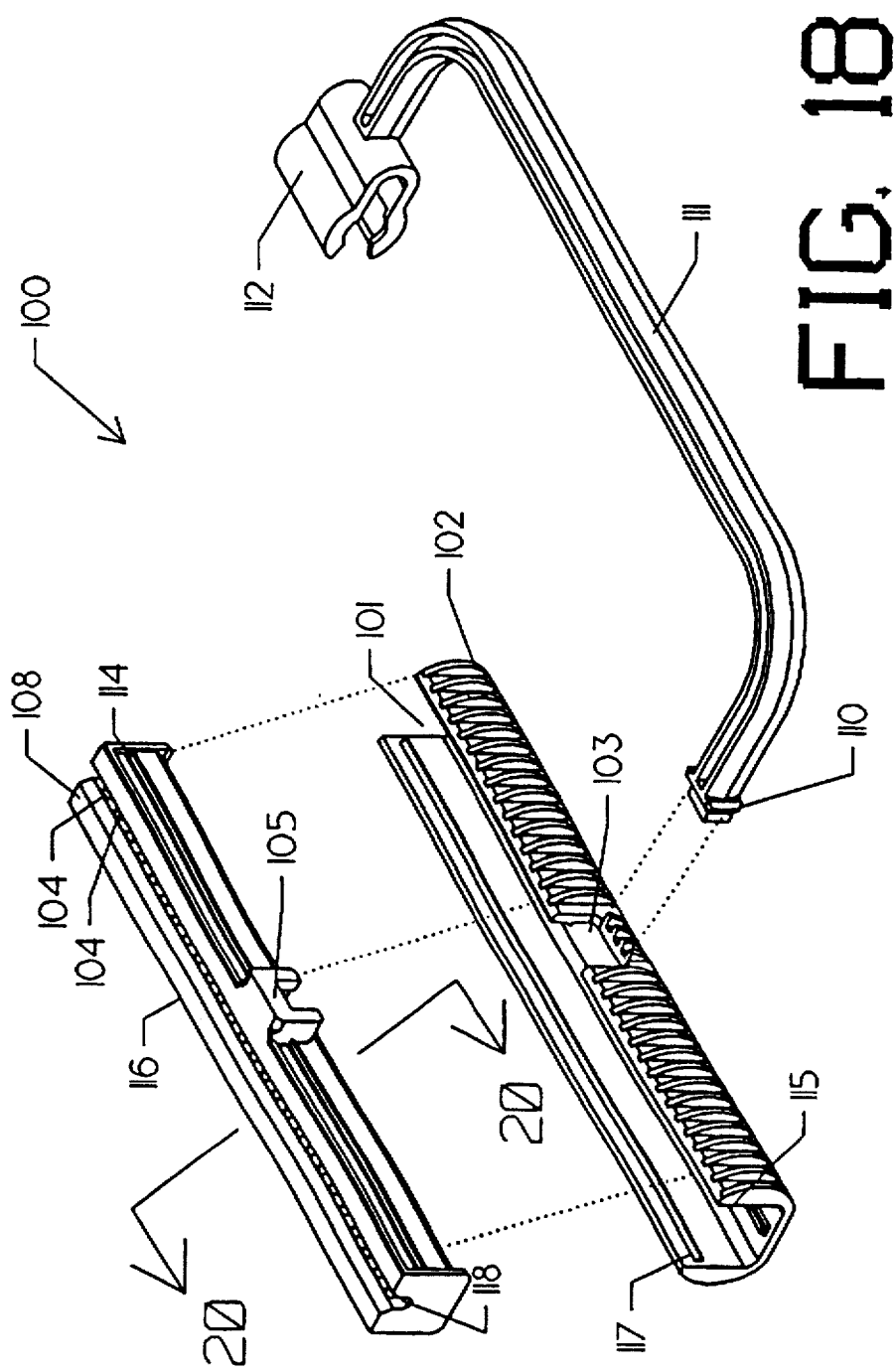
FIG. 18 is an exploded view of the three major components of the tool of an alternative embodiment.

The three major components of an alternative embodiment of the tool are shown in exploded view 100 in FIG. 18. Magnet fixture block 108 receives permanent magnets (not shown) in magnet receiving slots 104 as described above. Preferably, the magnets are placed with alternating polarity to increase the effective axial holding force and decrease the effective normal force which reduces longitudinal friction. Magnet fixture block 108 is preferably molded of a polycarbonate, with General Electric Lexan HP2X-42046 being the recommended material.

Bottom block 102 is molded of a similar but clear material, such as General Electric Lexan HP2X-111, and engages with magnet fixture block 108, through receiving channel 101. In operation, magnet fixture block 108 is held within receiving channel 101 by the engagement of longitudinal protrusions 116 and 114 of magnetic fixture block 108 within longitudinal channels 115 and 117 of bottom block 102, respectively. Configured catheter receiving notch 118 stabilizes the position of the catheter assembly as discussed in greater detail below.

Operator handle 111 is molded of Lexan HP2X-111 (clear) material. It has a catheter receiving element 112 and a configured engagement latch 110, which is fixedly engaged within receiving notch 103 of bottom block 102 and receiving notch 105 of magnet fixture block 108.

Figure 19:
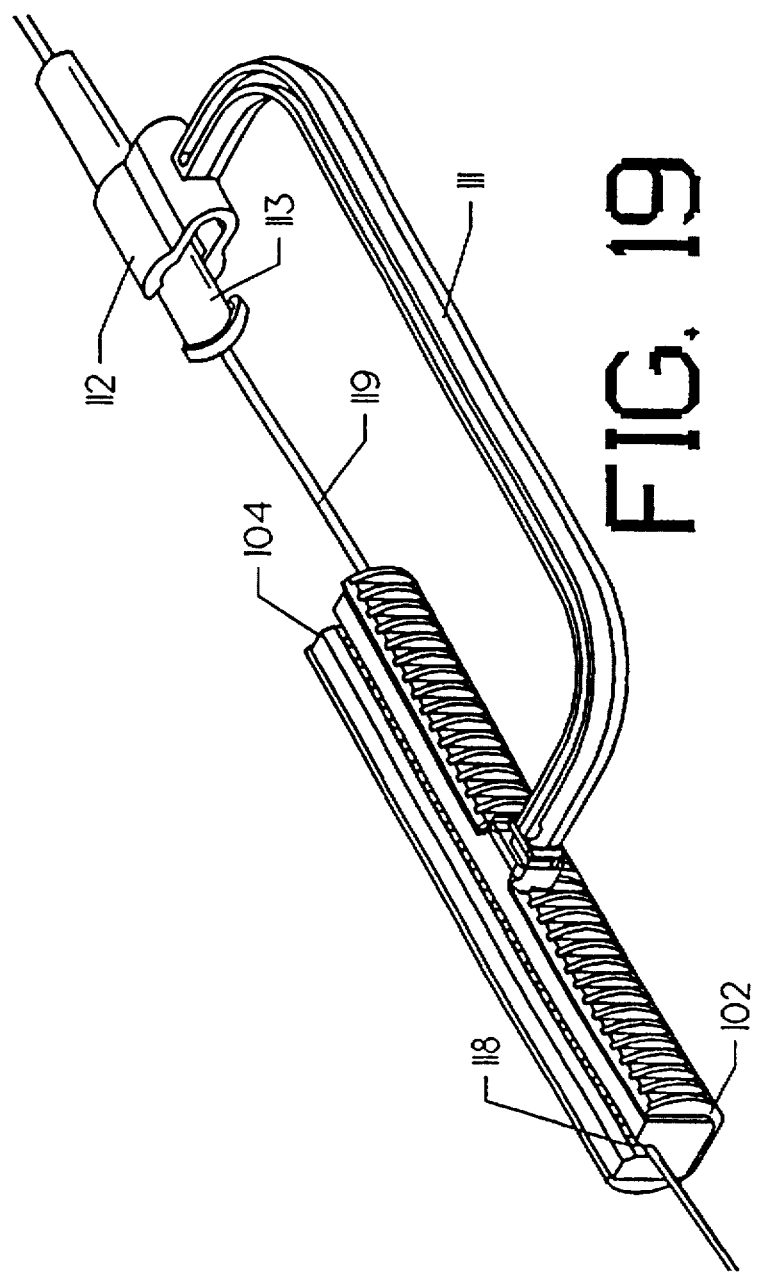
FIG. 19 is an isometric view of the operation of the alternative embodiment of FIG. 18.

FIG. 19 is a isometric composite view of the alternative embodiment of FIG. 18 in operation. Catheter receiving element 112 slidably engages y-adapter 113 of catheter assembly 119 as shown. Catheter assembly 119 is stabilized within configured catheter receiving notch 118. The operator conveniently grasps the entire assembly using handle 111.

Figure 20:
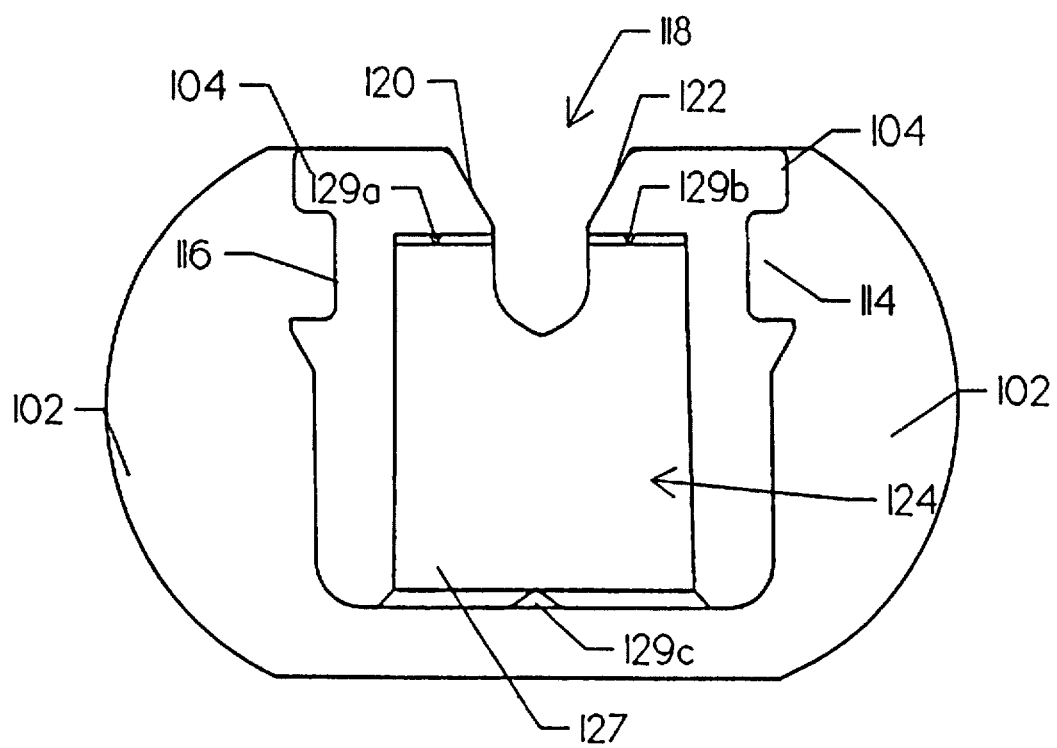
FIG. 20 is a close up view of the catheter receiving notch of the alternative embodiment.
Figure 21:
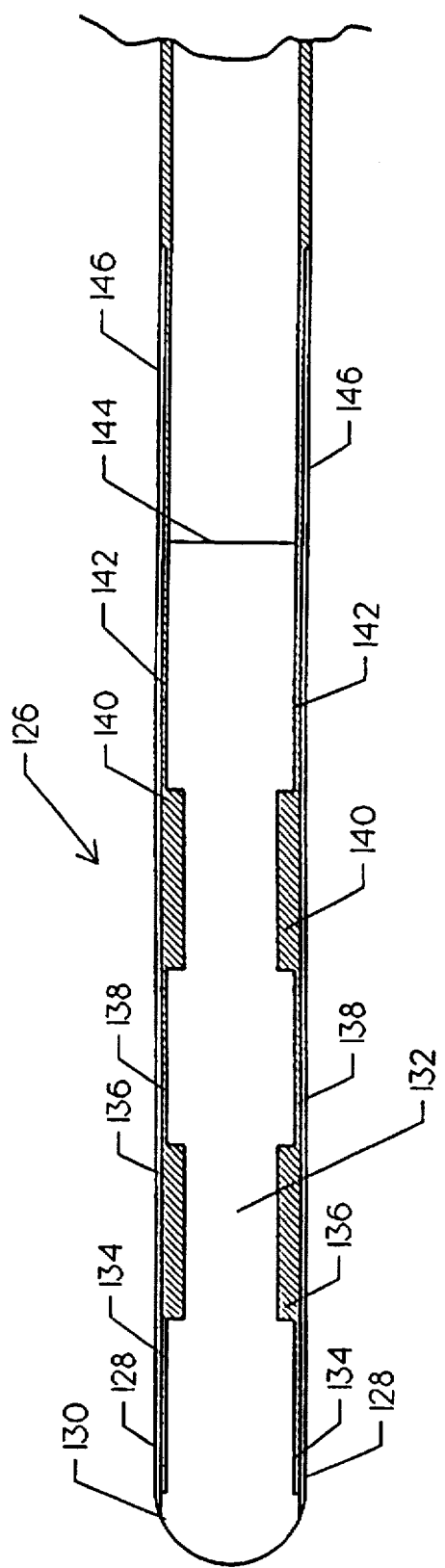
FIG. 21 is a longitudinally sectioned view of the proximal end of the guide wire of the preferred embodiment.

A cross sectional view of the assembled tool is shown in FIG. 20. Inclines 120 and 122 direct catheter assembly 119 into catheter stabilization channel 118, which is configured to hold catheter assembly 119 within the above described magnetic field. Permanent magnet 127 is shown held in place by contact with molded spikes 129a, 129b, and 129c.

An alternative embodiment of the proximal end of guide wire active area 126 is shown in longitudinal sectioned view 21. The inner core 132 of the assembly is preferably a wire of Hiperco 50B, which is an alloy of approximately 48.5% cobalt, 48.5% iron, 3% vanadium, and trace elements. It is commercially available as explained above and has a diameter of about 0.011 inch.

Inner core 132 is circumferentially ground to produce a reduced diameter of about 0.0045 inch for a distance of about 0.075 inch at areas 136 and 140, which are separated by distance 138, also about 0.075 inch. Proximal distance 134 is about 10.075 inches, and distance 142 is about 0.5 inch. The proximal end of a standard spring coil guide (not shown for clarity) is butt welded to distal end 144 of inner core 132.

Inner core 132 is coated with an adhesive, which is preferably Hysol 9412 to fill the ground areas 136 and 140 to an overall depth at the unground areas of about 0.001 inch. The resulting structure has a uniform outside diameter of about 0.011 inch, which is covered before curing is completed by hypotubing 128 of 304 stainless steel. The wall thickness of hypotubing 128 is chosen to provide a standard finished outside diameter, such as 0.018 or 0.014 inch. Hypotubing 128 extends distally of distal end 144 of inner core 132 by at least 0.5 inch along area 146 to provide strain relief to the butt weld at distal end 144. Proximal end 130 is ground to a smooth hemispherical shape.

Figure 17:
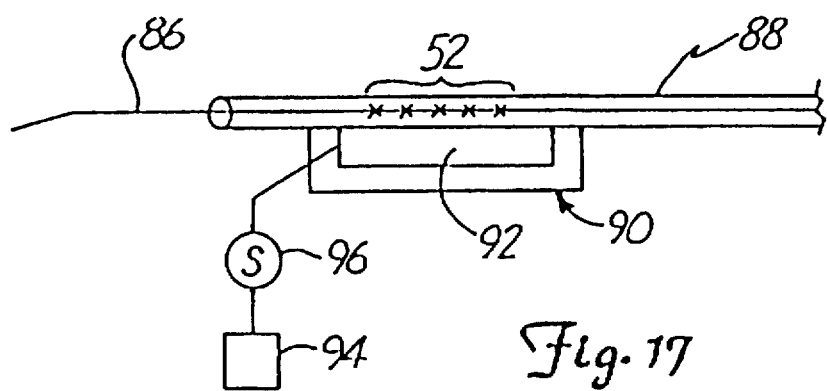
FIG. 17 is a schematic illustration of a tool which includes an electromagnet.

Another way to selectively apply a magnetic field between the operative segment of the guide wire and the tool is to form the magnet on the tool as an electromagnet. As illustrated diagrammatically in FIG. 17, a guide wire (or guide wire extension) 86 includes an operative segment 52 (as previously described) and the guide wire 86 is, in use, inserted within a lumen of a catheter 88. A tool 90 in this embodiment includes an electromagnet 92 which has selectively activated sections therein aligned to cooperate within the operative segment 52, and which is connected to a current source 94 through an on/off switch 96. Operation of the switch 96 thus controls the application of current to the electromagnet 92 and the creation of a magnetic field thereby. The selectively activated sections within the tool 90 may be energized by wall current (AC) or rectified wall current (DC), either of which can be turned off by switch 96 to break the holding force between the tool 90 and the guide wire 86.

It is also contemplated that alternate forms of coupling forces may be used in the present invention. For instance, instead of using permanent magnets or electromagnets, the coupling force field between the guide wire and the captivation tool may be generated by the use of electrostatic or electric fields. In each case, the coupling force between the tool and the guide wire can operate through the catheter body, and there is no contact required between the tool and the guide wire.

Alternative embodiments of the guide wire 36 operative segment are shown generally at 150 in FIGS. 22–28. In these embodiments, the operative segment 150 can be similar to the previously described operative segment 52 and guide wire active area 126. The embodiment shown in FIGS. 22–28 improve overall guide wire 36 reliability with improved structural reinforcement. The use of these embodiments results in improved performance of the operative segment 150 and improved overall performance of the guide wire 36 in catheter exchange procedures.

Figure 22:
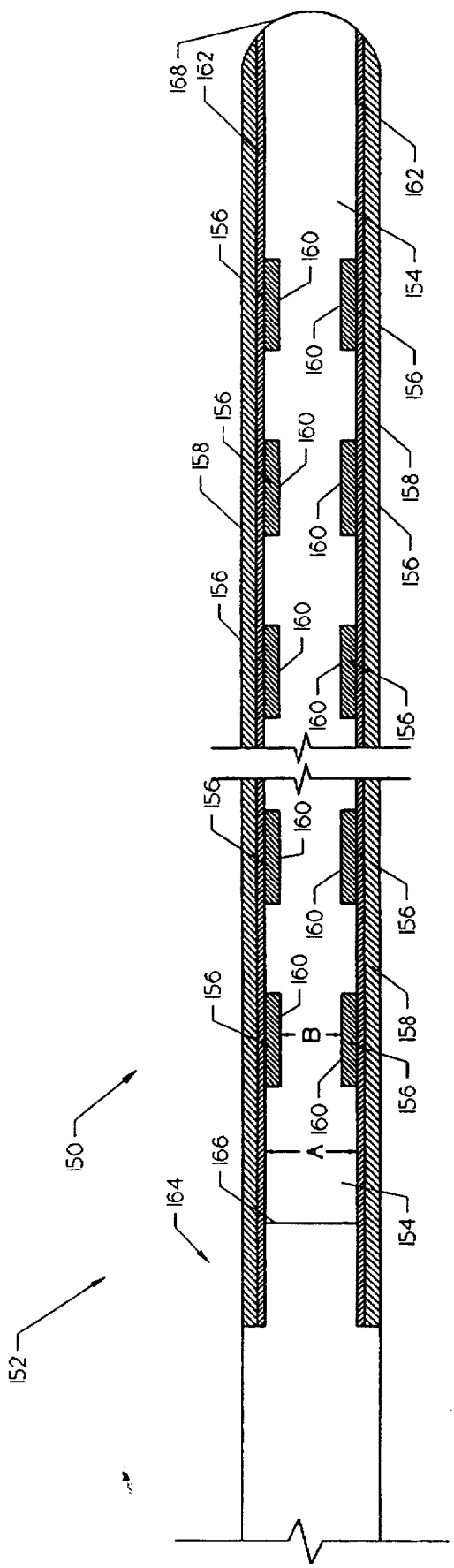
FIG. 22 is a detailed sectional view of an operative segment of a guide wire which is another preferred embodiment of the present invention.

Referring to FIG. 22, the distal end of guide wire 36, including operative segment 150, is shown generally at 152. Operative segment 150 includes a core 154, metallic segments 156 and a tubular member 158. Metallic segments 156 are located within notched areas 160 of core 154. Tubular member 158 surrounds core 154, and has an outside diameter approximately equal to the outside diameter of the overall guide wire 36.

Core 154 is formed of a highly paramagnetic material relative to the rest of operative segment 150, and becomes highly magnetic when subjected to a magnetic field. In a preferred embodiment, the core 154 is formed of Hiperco 50B, which is an alloy of approximately 48.5% cobalt, 48.5% iron, 3% vanadium, and trace elements.

Core 154 is formed by first pulling the Hiperco material through a heated dye to form a Hiperco wire. The Hiperco wire is ground to a desired uniform outside dimension.

Core 154 is notched in equally spaced areas longitudinally along core 154. In one preferred embodiment, core 154 is notched by a centerless grinding process in which the Hiperco wire is held stationary while a wheel rotates about the wire for precision grinding each notch. In one preferred embodiment, operative segment 150 includes approximately 180 notched segments 160, which are approximately 0.040 inches in length and 0.003 inches in depth. These dimensions are common to the operative segment 150 of FIGS. 22–28.

Referring again to FIG. 22, notched core 154 includes a larger major diameter A, and a smaller minor diameter B which together define the notched segments 160. A metal substance is filled within notched segments 160 to form metallic segments 156. The metal substance occludes the space within the notched segment 160, such that core 154, including metallic segments 156, is now formed of a uniform outer diameter equal to major diameter A.

Metallic segment 156 is formed of a metallic substance which is non-paramagnetic or substantially less paramagnetic than the highly paramagnetic core 154. The operative segment 150, including a core 154 having a plurality of metallic segments 156, results in a magnetic "edge effect" at each notched corner. This results in an operative segment having a very strong magnetic field in a direction longitudinal to the core 154, and a relatively weak magnetic field in a radial direction relative to the core 154.

A tubular member 158 is placed over core 154. In a preferred embodiment, the tubular member 158 is formed of a stainless steel hypotube having an outside diameter approximately equal to the outside diameter of the remaining portion of guide wire 36, and an inside diameter which is 0.0005 inches greater than the core 154 major diameter A. The tubular member 158 may be placed over core 154 while located in an adhesive bath for securing the tubular member 158 to the core 154. In a preferred embodiment, the adhesive bath is Hysoll™ adhesive, available from Dexter Co., which forms the adhesive layer 162 shown between tubular member 158 and core 154. The adhesive which forms around the outside diameter of tubular member 158, is removed.

Operative segment 150 is completed by center grinding the distal end 164 of operative segment 150 to complement a ground portion of the distal end of guide wire 36. Operative segment 150 is then securely attached to guide wire 136 by known means, such as a resistance weld, indicated at 166. Additionally, the proximal end 168 of operative segment 150 is ground smooth.

Operative segment 150 provides improved structural reinforcement, resulting in a higher performance guide wire 36. By combining metallic segments 156 with magnetically permeable core 154, an operative segment 150 is formed having greater structural integrity similar to that of a solid core wire, while retaining the response necessary for use with a magnetic exchange device system.

In one preferred embodiment, the metallic segments 156 are formed of a brazeable/solderable material. Preferably, the braze/solder is formed of silver, although it is recognized that it may be formed of other brazeable/solderable materials such as tin or other metal or metal blends. The metallic segments 156 are formed on core 154 by pulling the notched core 154 through a bath of high-temperature solder/braze, the braze/solder having a lower melting temperature than core 154. With this method, the notches within core 154 are filled with brazeable/solderable material to form metallic segments 156. After cooling, core 154 may be ground to major diameter A, or alternatively, pulled through a shaping dye to provide core 154 with a uniform outside diameter along the longitudinal operative segment 150.

In yet another embodiment, metal segments 156 are formed of an electroless metallic substance such as electroless nickel or electroless chrome. The metallic substance is filled within the notched core 154 notched segments 160 by locating the core 154 in an electroless solution with a metal such as nickel. The solution temperature is elevated to activate the solution, such that the nickel ions adhere to core 154 and specifically notched segments 160 to form metallic segments 156. Core 154 is then centerless ground to a uniform outer diameter.

Alternatively, metal segments 156 may be formed by electrolytic plating of a metal substance on core 154. The electrolytic plating is accomplished by first passing core 154 through a clean bath solution to prepare the core 154 surface for electrolytic plating. The clean bath contains an electrochemical cleaning solution mixture which may include a mixture of sodium hydroxide and water. The electrochemical cleaning solution electrically scrubs the surface of notched core 154. A power supply is provided for providing a positive charge to the notched core 154 and a negative charge to the clean bath enclosure. In operation, as power is supplied to the clean bath, unwanted materials flow away from the positively charged notched core 154 due to electrolytic cleaning action.

Upon completion of the clean bath process, the core 154 passes through a water rinse containing deionized water. The deionized water rinses away unwanted particles from notched core 154. Specifically, the water rinse contains clean and filtered water that rinses away contaminants which may effect the electrical conductivity of core 154.

Next, operating segment 150 routes through a strike bath for providing a thin layer of metallic substrate on core 154, and more importantly, notched segments 160. The strike bath process generally includes an electrolytic bath, a metal anode, and a power supply having a positive terminal and a negative terminal.

The electrolytic bath includes an electro-chemical solution, such as a mixture of nickel chloride, hydrochloric acid and deionized water. The anode is located within the electrolytic bath. The anode is formed of a metal or a mixture of metals, such as nickel, tin, stainless steel or copper. In a preferred embodiment, the anode is formed of 99.95% pure nickel.

In the strike bath, the power supply positive terminal is electrically coupled to the anode. The power supply negative terminal is electrically coupled to the notched core 154. The notched core 154 may be located stationary within the strike bath, or may move through the strike bath as part of one continuous core 154.

When power is supplied to the strike bath, positively charged nickel atoms are attracted to and flow to the negatively charged core 154. The nickel atoms attach themselves to the core 154, forming a thin layered metallic substrate on the surface of core 154, including within notched segments 160. The thin metallic substrate formed of nickel allows for adherence of a greater mass of nickel to be plated on core 154, and specifically, to fill notched segments 160 in the next plating bath process step.

Next, core 154 is passed through a plate bath process which is similar to the previous strike bath process. The plate bath also includes a power supply having a positive terminal and a negative terminal, a plate bath solution, and an anode. The plate bath plates a greater mass of nickel over core 154 than the previous strike bath, to fill the notched segments 160 to form the metallic segments 156. This is accomplished by increasing the power supplied to the plate bath process and by adapting the plating bath chemistry, both resulting in a greater amount of nickel flowing from the anode to the core 154. After leaving the plate bath, the plated core 154 again passes through a deionized water rinse. Finally, the core 154, including plated metallic segments 156, is ground to the desired size having a uniform outer diameter.

In an alternative process, the metallic segments 156 of core 154 may be formed through a sputtering process. The sputtering process is performed within a vacuum where the notched core 154 is placed at a target position within the vacuum. Sputtered metal is then introduced as a fine powder or spray to the notched core 154 by blasting a selected metal cube with an energy wave or beam. The selected metal spray evenly deposits in a thin film on the core 154. In one preferred embodiment, the sputtered metallic substance is copper. The metallic substance would be sputtered onto core 154 filling in the notched areas, until the notched segments 160 minor diameter equals the major diameter of the core 154. Upon completion of the sputtering process, core 154 would be ground to one uniform diameter.

Figure 23:
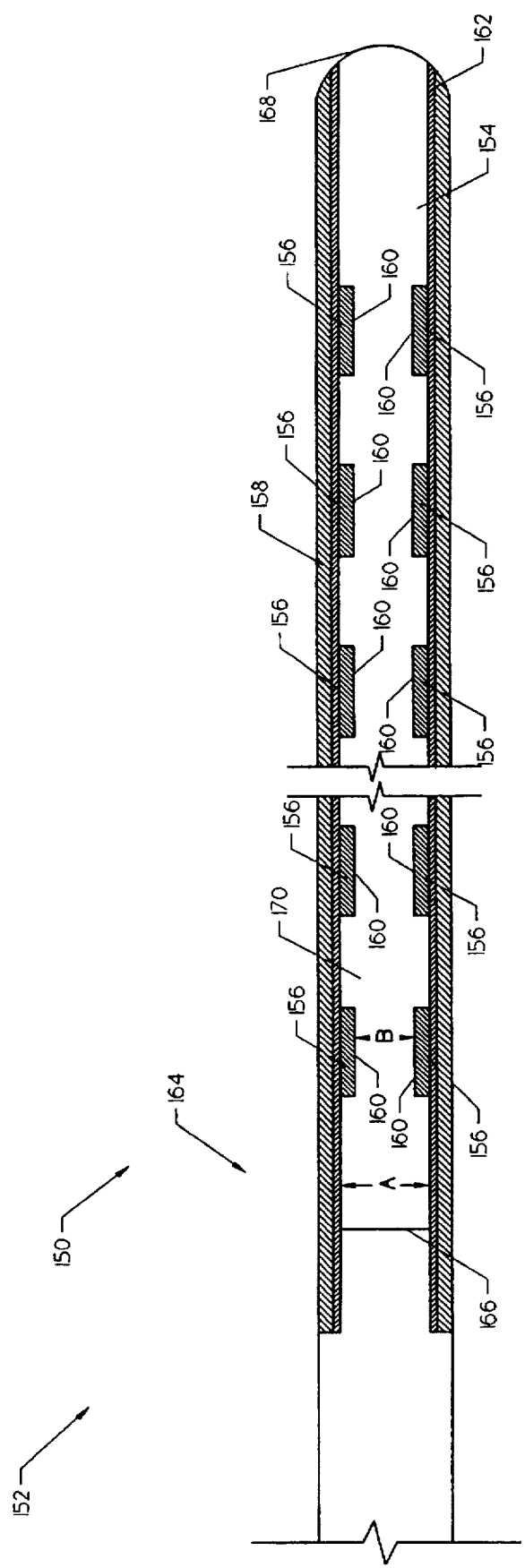
FIG. 23 is a detailed sectional view of an operative segment of a guide wire which is another preferred embodiment of the present invention.

Referring to FIG. 23, an alternative embodiment of the present invention is generally shown, which is similar to the operative segment of FIG. 22. Operative segment 150 includes a core 154 which is formed of non-paramagnetic or very low paramagnetic material. Using processes previously described in this application, the notched segments 160 of non-paramagnetic core 154 are plated with a metallic substance to a sufficient depth to fill the minor diameter B of notched segments 160 to equal the major diameter A of core 154. The metallic substance is formed of a paramagnetic or highly paramagnetic material to provide the attraction of the operative segment 150 to the ancillary magnetic exchange device. The core 154 is then centerless ground to the desired uniform major diameter A. Ground core 154 is placed in an adhesive bath for securing tubular member 158 over core 154 with an adhesive layer 162. In a preferred embodiment, the tubular member 158 is a hypotube.

The present invention provides increased structural reinforcement of the proximal portion of magnetic guide wires, and more specifically, operative segment 150. Additionally, the present embodiment provides torqueability and pushability similar to a solid guide wire.

Figure 24:
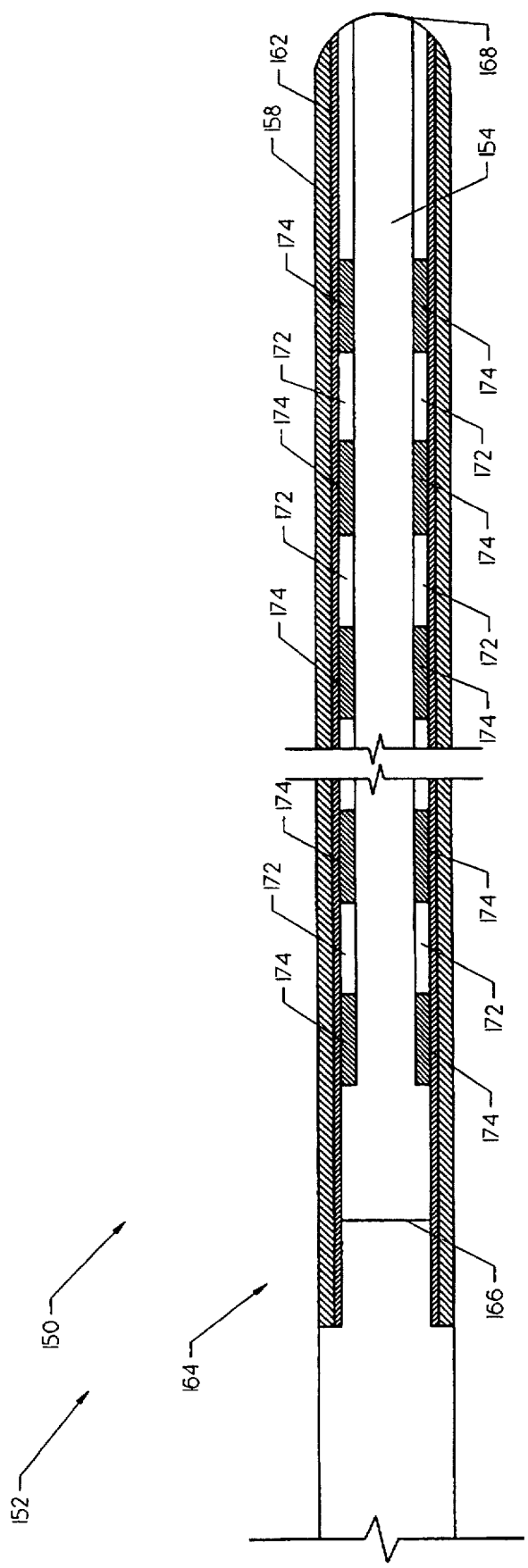
FIG. 24 is a detailed sectional view of an operative segment of a guide wire which is another preferred embodiment of the present invention.

Another alternative embodiment of operative segment 150 is shown in FIG. 24. In this embodiment, core 154 is formed of a solid metallic core. In a preferred embodiment, core 154 is formed of solid stainless steel, having a uniform outside diameter. The solid stainless steel core 154 is covered with alternating sleeves, which include sleeves 172 formed of non-paramagnetic material and sleeves 174 formed of a highly paramagnetic material. The alternating sleeves 172 and 174 are then coated with an adhesive layer 162 for adherence. In another instance, tubular member 158 may be placed over the alternating sleeves 172 and 174, secured to the sleeves by adhesive layer 162.

Figure 25:
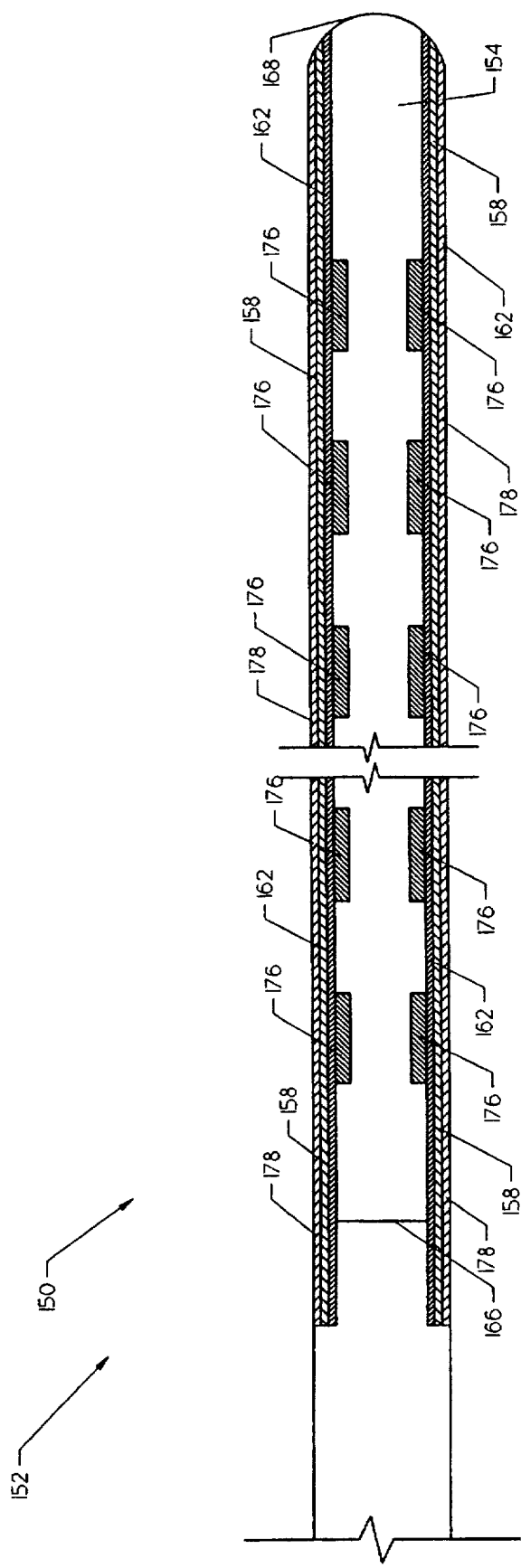
FIG. 25 is a detailed sectional view of an operative segment of a guide wire which is another preferred embodiment of the present invention.

Referring to FIG. 25, an alternative embodiment of operative segment 150 is shown. Core 154 notched segments 160 may be filled with a non-metallic substance, such as epoxy or a metallic substance, such as nickel, tin, silver or copper by processes previously described in this application. Notched segments 160 are filled to bring the minor diameter B of the notched segments 160 equal to the major diameter A of core 154, as shown at 176. Next, a thin walled tubular member 158 is placed over the core 154. In a preferred embodiment, the thin walled tubular member 158 is formed of a 304 stainless steel hypotube, which is secured to the core 154 by an adhesive layer 162. The thin walled tubular member 158 is coated with a metallic layer 178.

In a preferred embodiment, the metallic layer 178 is formed of a material having superelastic resilient properties, such as Nitinol. Although it is recognized that other processes may be used, in a preferred embodiment, Nitinol is sputter coated on thin tubular member 158 to form metallic layer 178. Alternatively, metallic layer 178 may be formed of a non-metallic material, such as a polymeric material.

This unique embodiment of the present invention gives operative segment 150 the physical advantages of both the stainless steel hypotube and the Nitinol coating. Specifically, the present operative segment 150 invention has the advantages of the superelastic resilient properties of Nitinol and the pushability and torqueability of the stainless steel hypotube.

Figure 26:
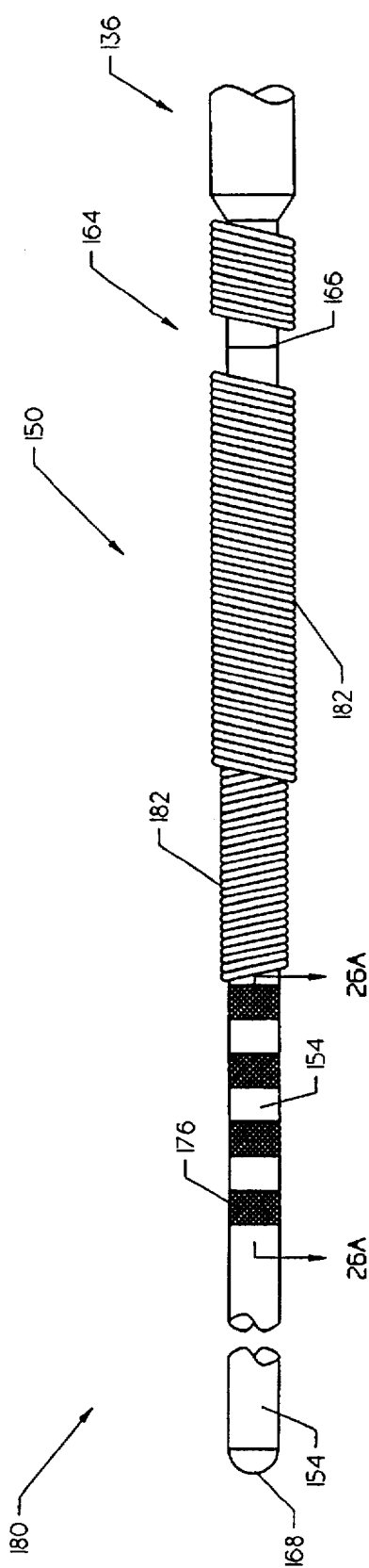
FIG. 26 is a fragmented perspective view of an operative segment of a guide wire which is another preferred embodiment of the present invention.

Referring to FIG. 26, an alternative embodiment of operative segment 150 is shown in partial perspective view generally at 180. Operative segment 150 includes at least one stranded layer. In one preferred embodiment, operative segment 150 is multi-layered, including multiple stranded layers for improved structural reinforcement and overall guide wire performance.

Figure 26A:
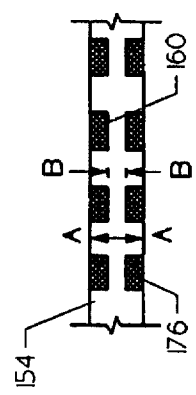
FIG. 26A is a detailed partial sectional view of the operative segment shown in FIG. 26.

FIG. 26A is a sectional view of core 154 having filled notched segments 160. Operative segment 150 includes a core 154 having notched segments 160. Notched segments 160 are filled with a material 176, such as epoxy resin, bringing the minor diameter B of notched segments 160 equal to the major diameter A of core 154.

Next, operative segment 150 includes multiple layers of strands 182 tightly wrapped around core 154. In a preferred embodiment, the strands 182 are formed of stainless steel ribbons or composite fibers filled with epoxy resin. Each layer 182 may be tightly wrapped around core 154 in an alternate direction to give core 154 additional structural integrity. The tightly wrapped stranded layers 182 are brought to a diameter equal to that of the outside diameter of guide wire 36.

The multiple stranded layers 182 of the present invention increase the structural reinforcement of operative segment 150 necessary for efficient use in catheter exchange systems. Additionally, the stranded layers provide for efficient pushability and torqueability of guide wire 36.

Figure 27:
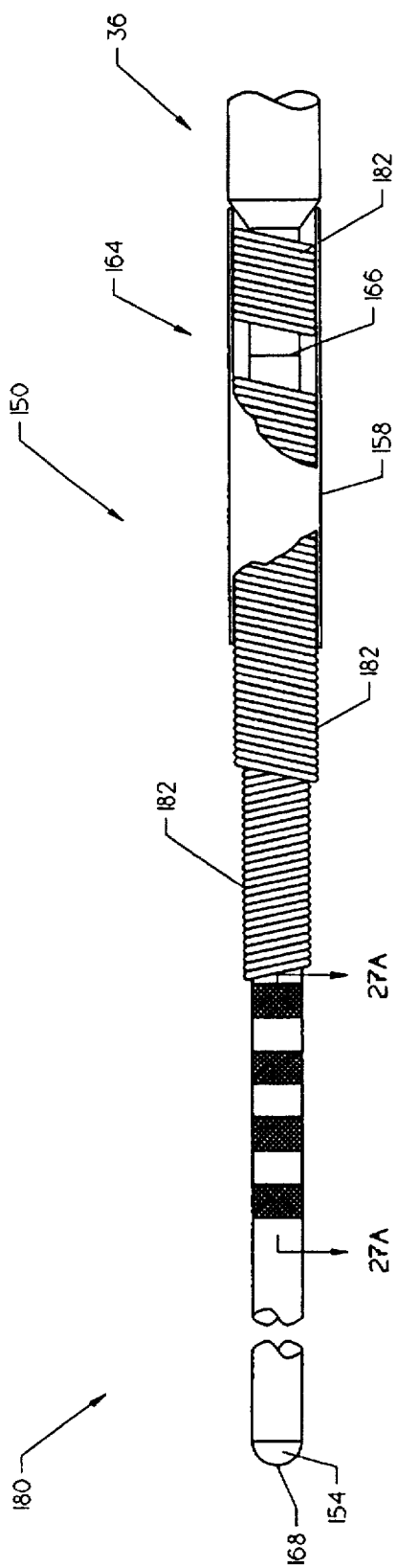
FIG. 27 is a fragmented perspective view of an operative segment of a guide wire which is another preferred embodiment of the present invention.
Figure 27A:
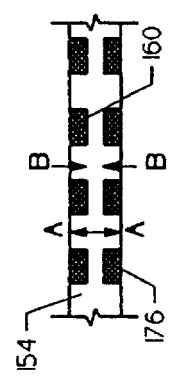
FIG. 27A is a detailed partial sectional view of the operative segment shown in FIG. 27.

FIGS. 27 and 27A show an alternative embodiment of the operative segment 150 shown in FIGS. 26 and 26A. In this embodiment, an additional tubular member 158, shown broken away, is placed over the multi-layered strands 182. In a preferred embodiment, the tubular member 158 is formed of a stainless steel hypotube. The tubular member 158 provides increased pushability and torqueability performance of operative segment 150 and guide wire 36. Additionally, the tubular member 158 may be coated with a lubricous material for a smooth surface.

Figure 28:
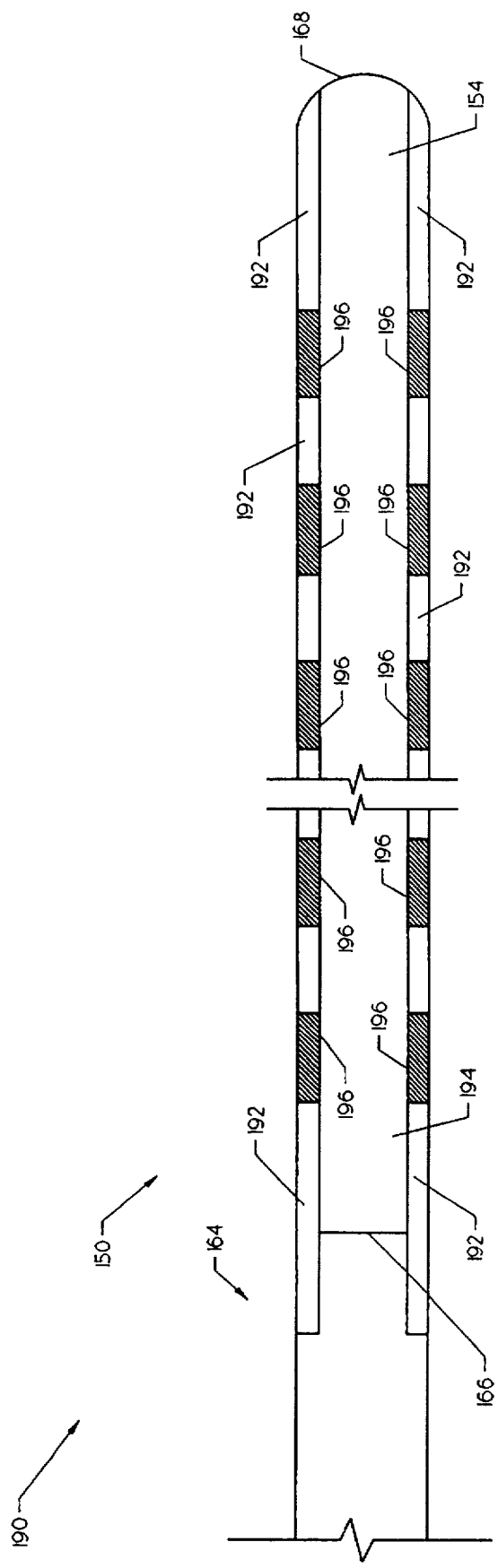
FIG. 28 is a detailed sectional view of an operative segment of a guide wire which is another preferred embodiment of the present invention.

FIG. 28 shows yet another embodiment of the present operative segment 150 invention generally at 190. In this embodiment, operative segment 150 is formed by forming a highly paramagnetic layer 192 over a non-paramagnetic or low paramagnetic core 154. In a preferred embodiment, the non-paramagnetic core is a stainless steel wire having a uniform outside diameter. The highly paramagnetic layer 192 is formed of Hiperco which is extruded over core 154. Alternatively, non-paramagnetic core 154 with highly paramagnetic layer 192 may be formed through a co-extrusion process. Next, slots 196 are ground through or almost through the highly paramagnetic layer 192. The slots 196 are then filled with a substance 198 to bring the outside diameter of the slots 196 up to the major diameter of the core 154. In a preferred embodiment, the slots 196 are filled with polymer, although it is recognized that the slots may be filled with other metallic or non-metallic substances such as those previously described in this application.

The surface of operative segment 150 is now finished by a final grinding process. The surface of operative segment 150 to an outside uniform diameter equal to the outside diameter of the guide wire 36.

The present embodiment of the operative segment 150 invention provides increased structural reinforcement, while improving the overall performance of the operative segment. Specifically, by placing a highly paramagnetic material on the outside diameter of operative segment 150, a greater attraction is achieved between the operative segment 150 and the magnetic exchange device or ancillary tool during a catheter exchange procedure.

Additionally, providing a non-paramagnetic, solid stainless steel core places the solid stainless steel at a position where it is most mechanically effective for improving structural integrity of the operative segment 150. By placing the highly paramagnetic layer on the outside diameter of the operative segment 150, resulting in an increased attractive force, less magnetic segments may be necessary for maintaining the necessary longitudinal holding force between the operative segment 150 and the magnetic exchange device or ancillary tool.

Although the present invention has been described with reference to preferred embodiments, workers skilled in the art will recognize that changes may be made in form and detail without departing from the spirit and scope of the invention.

What is claimed is:

1. A catheter apparatus comprising:

a guidewire including a shaft including a plurality of notches and a metallic material located within the notches which is less magnetically permeable than the shaft into which the notches are formed; and a tool including a plurality of magnets spaced for coupling with the metallic material disposed in the notches.

2. An apparatus in accordance with claim 1, wherein the metallic material is a brazable material.

3. An apparatus in accordance with claim 1, wherein the metallic material is a solderable material.

4. An apparatus in accordance with claim 1, further comprising a tubular member located around the shaft.

5. The apparatus in accordance with claim 4, further comprising an adhesive layer located between the tubular member and the shaft.

* * * * *